US011218321B2

(12) United States Patent
Meriac et al.

(10) Patent No.: US 11,218,321 B2
(45) Date of Patent: Jan. 4, 2022

(54) METHODS OF ACCESSING AND PROVIDING ACCESS TO DATA SENT BETWEEN A REMOTE RESOURCE AND A DATA PROCESSING DEVICE

(71) Applicant: ARM IP LIMITED, Cambridge (GB)

(72) Inventors: Milosch Meriac, Cambridge (GB); Geraint Luff, Cambridge (GB)

(73) Assignee: ARM IP LIMITED, Cambridge (GB)

( * ) Notice: Subject to any disclaimer, the term of this patent is extended or adjusted under 35 U.S.C. 154(b) by 0 days.

(21) Appl. No.: 15/315,659

(22) PCT Filed: May 29, 2015

(86) PCT No.: PCT/GB2015/051564

§ 371 (c)(1),
(2) Date: Dec. 1, 2016

(87) PCT Pub. No.: WO2015/185893

PCT Pub. Date: Dec. 10, 2015

(65) Prior Publication Data

US 2017/0187536 A1 Jun. 29, 2017

(30) Foreign Application Priority Data

Jun. 3, 2014 (GB) ..................................... 1409853
Nov. 12, 2014 (GB) ..................................... 1420101

(51) Int. Cl.
*H04L 9/32* (2006.01)
*G06F 21/62* (2013.01)
(Continued)

(52) U.S. Cl.
CPC ........ *H04L 9/3247* (2013.01); *G06F 12/0813* (2013.01); *G06F 16/252* (2019.01);
(Continued)

(58) Field of Classification Search
CPC . H04L 9/3247; H04L 9/14; H04L 9/30; H04L 9/3263; H04L 63/0428;
(Continued)

(56) References Cited

U.S. PATENT DOCUMENTS 5,708,780 A 1/1998 Levergood et al.
6,154,811 A 11/2000 Srbljic et al.
(Continued)

FOREIGN PATENT DOCUMENTS

CN 101645827 A 2/2010
CN 102624881 A 8/2012
(Continued)

OTHER PUBLICATIONS

Kalarani et al., "Improving the efficiency of retrieved result through transparent proxy cache server," 2013 Fourth International Conference on Computing, Communications and Networking Technologies (ICCCNT) Year: 2013 | Conference Paper | Publisher: IEEE.*
(Continued)

*Primary Examiner* — Roderick Tolentino
(74) *Attorney, Agent, or Firm* — Patterson Thuente Pedersen, P.A.

(57) ABSTRACT

A method of accessing data sent between a remote resource and a data processing device, the method comprising: caching data uploaded from the remote resource or caching data sent to the remote resource at one or more intermediate network nodes between the data processing device and the remote resource; and accessing the cached data stored at the one or more intermediate network nodes.

19 Claims, 11 Drawing Sheets

(51) Int. Cl.

| | |
|---|---|
| ***G06F 16/25*** | (2019.01) |
| ***G06F 16/955*** | (2019.01) |
| ***H04L 29/08*** | (2006.01) |
| ***G16Z 99/00*** | (2019.01) |
| ***H04L 29/06*** | (2006.01) |
| ***G06F 12/0813*** | (2016.01) |
| ***H04L 9/14*** | (2006.01) |
| ***H04L 9/30*** | (2006.01) |
| ***G16H 10/65*** | (2018.01) |
| ***G16H 80/00*** | (2018.01) |

(52) U.S. Cl.

CPC ...... *G06F 16/9566* (2019.01); *G06F 21/6209* (2013.01); *G06F 21/6245* (2013.01); *G16H 10/65* (2018.01); *G16H 80/00* (2018.01); *G16Z 99/00* (2019.02); *H04L 9/14* (2013.01); *H04L 9/30* (2013.01); *H04L 9/3263* (2013.01); *H04L 63/0428* (2013.01); *H04L 63/101* (2013.01); *H04L 63/166* (2013.01); *H04L 67/02* (2013.01); *H04L 67/2842* (2013.01); *G06F 2212/154* (2013.01); *G06F 2212/60* (2013.01); *G06F 2212/62* (2013.01); *G06F 2221/2107* (2013.01); *G06F 2221/2119* (2013.01); *H04L 63/067* (2013.01); *H04L 63/08* (2013.01); *H04L 63/168* (2013.01)

(58) Field of Classification Search

CPC ... H04L 63/101; H04L 67/2842; H04L 67/02; H04L 63/166; H04L 63/08; H04L 63/067; H04L 63/168; H04L 61/2539; H04L 63/04; H04L 63/12; G06F 12/0813; G06F 21/6245; G06F 2212/154; G06F 2212/60; G06F 2212/62; G06F 2212/02; G06F 16/252; G06F 16/9566; G06F 19/00; G06F 21/6209; G06F 2221/2107; G06F 2221/2119; G06F 16/9574; G06F 16/13; G06F 16/172; G06F 9/45533; G06F 12/0806; G06F 9/52; G16H 10/65; G16H 80/00

See application file for complete search history.

(56) References Cited

U.S. PATENT DOCUMENTS

| | | | | |
|---|---|---|---|---|
| 6,195,680 | B1 | 2/2001 | Goldszmidt et al. | |
| 6,823,377 | B1 | 11/2004 | Wu et al. | |
| 7,363,361 | B2 | 4/2008 | Tewari et al. | |
| 7,698,269 | B2 | 4/2010 | Zhou et al. | |
| 8,479,298 | B2 | 7/2013 | Keith et al. | |
| 9,166,979 | B2 * | 10/2015 | Hoard | H04L 63/10 |
| 9,471,533 | B1 * | 10/2016 | Roth | G06F 15/167 |
| 9,544,351 | B1 * | 1/2017 | Lee | H04L 67/1097 |
| 9,887,970 | B2 | 2/2018 | Luff et al. | |
| 2003/0097564 | A1 | 5/2003 | Tewari et al. | |
| 2003/0105807 | A1 | 6/2003 | Thompson et al. | |
| 2003/0217163 | A1 | 11/2003 | Lagerweij et al. | |
| 2004/0215755 | A1 * | 10/2004 | O'Neill | G06F 8/654 709/223 |
| 2006/0106802 | A1 | 5/2006 | Giblin et al. | |
| 2006/0181928 | A1 | 8/2006 | Lee et al. | |
| 2007/0136279 | A1 | 6/2007 | Zhou et al. | |
| 2009/0193513 | A1 | 7/2009 | Agarwal et al. | |
| 2011/0082946 | A1 * | 4/2011 | Gopalakrishnan | H04L 67/2828 709/231 |
| 2011/0131408 | A1 | 6/2011 | Cook et al. | |
| 2012/0030774 | A1 | 2/2012 | Keith et al. | |
| 2012/0076052 | A1 | 3/2012 | Kling et al. | |
| 2012/0089781 | A1 | 4/2012 | Ranade et al. | |
| 2012/0124372 | A1 * | 5/2012 | Dilley | H04L 63/0471 713/162 |
| 2012/0166592 | A1 * | 6/2012 | Elliot | H04L 67/2857 709/219 |
| 2012/0290677 | A1 | 11/2012 | Puthalath et al. | |
| 2013/0007239 | A1 * | 1/2013 | Agarwal | H04L 29/08 709/223 |
| 2013/0054514 | A1 * | 2/2013 | Barrett-Kahn | G06F 16/9574 707/608 |
| 2014/0019686 | A1 * | 1/2014 | Dong | G06F 12/0864 711/128 |
| 2016/0248587 | A1 * | 8/2016 | Westberg | H04L 63/0281 |
| 2016/0285961 | A1 * | 9/2016 | Kisel | H04L 67/2814 |
| 2017/0187536 | A1 | 6/2017 | Meriac et al. | |
| 2018/0115532 | A1 | 4/2018 | Luff et al. | |

FOREIGN PATENT DOCUMENTS

| | | | |
|---|---|---|---|
| CN | 103229181 | A | 7/2013 |
| CN | 103401950 | A | 11/2013 |
| EP | 2630610 | | 3/2013 |
| GB | 2510343 | A | 8/2014 |
| KR | 20060055314 | A | 5/2006 |

OTHER PUBLICATIONS

Chang et al., "The Implementation of a Web Crawler URL Filter Algorithm Based on Caching," 2009 Second International Workshop on Computer Science and Engineering Year: 2009 | vol. 2 | Conference Paper | Publisher: IEEE.*

International Preliminary Report on Patentability for corresponding International Application No. PCT/GB2015/051410, dated Dec. 15, 2016; 11 pages.

Search Report dated Nov. 12, 2015 for PCT Application No. PCT/GB2015/051410, 7 pages.

Written Opinion dated Nov. 12, 2015 for PCT Application No. PCT/GB2015/051410, 9 pages.

Search Report dated Nov. 18, 2014 for GB Application No. 1409853. 7, 5 pages.

Application and File history for U.S. Appl. No. 15/315,686, filed Dec. 1, 2016. Inventors: Luff et al.

International Preliminary Report on Patentability for corresponding International Application No. PCT/GB2015/051564 dated Dec. 15, 2016; 10 pages.

International Search Report for corresponding International Application No. PCT/GB2015/051564 dated Apr. 11, 2015; 7 pages.

Written Opinion for corresponding International Application No. PCT/GB2015/051564 dated Apr. 11, 2015; 8 pages.

Search Report for corresponding GB Application No. 1420101.6 dated May 15, 2015; 4 pages.

Application and File history for U.S. Appl. No. 15/850,550, filed Dec. 21, 2017. Inventors: Luff et al.

Office Action dated Apr. 1, 2019 for Chinese Application No. 201580029833.3, 20 pages.

Office Action dated Oct. 18, 2018 for Chinese Application No. 201580029342.9, 27 pages.

Office Action dated Sep. 3, 2019 for Chinese Application No. 201580029833,3, 12 pages.

Office Action dated Jun. 12, 2019 for Chinese Application No. 201580029342.9, 18 pages.

Office Action dated Mar. 27, 2020 for Chinese Application No. 201580029342.9, 24 pages.

Office Action dated Oct. 30, 2020 for Chinese Application No. 201580029342.9, 10 pages.

Examination Report dated Mar. 19, 2021 for GB Application No. 1420101.6, 2 pages.

Office Action dated Mar. 17, 2021 for Korean Application No. 1020167036923, 13 pages.

Examination Report dated Feb. 16, 2021 for GB Application No. 1420101.6, 3 pages.

Search Report dated Feb. 16, 2021 for GB Application No. 1420101. 6, 3 pages.

(56) References Cited

OTHER PUBLICATIONS

Search Report dated Sep. 22, 2020 for Application No. GB1420101.6, 5 pages.

* cited by examiner

Site secret

```
{
    "scope": "/data",          ← Secret applies to all subpaths of /data
    "url": {
        "secret": {"data": "a secret string", "encoding": "plain"},
        "hmac": "SHA256",
        "template": "/data/{hex:22}"
    },
    "content": {
        "key": {
            "data": "another secret string",
            "encoding": "plain"
        },
        "encryption": "AES192"
    },
    "keyExpansionUrl": "https://...."   ← Where to go for more site secrets
}
```

How to encode URL

How to encode document content

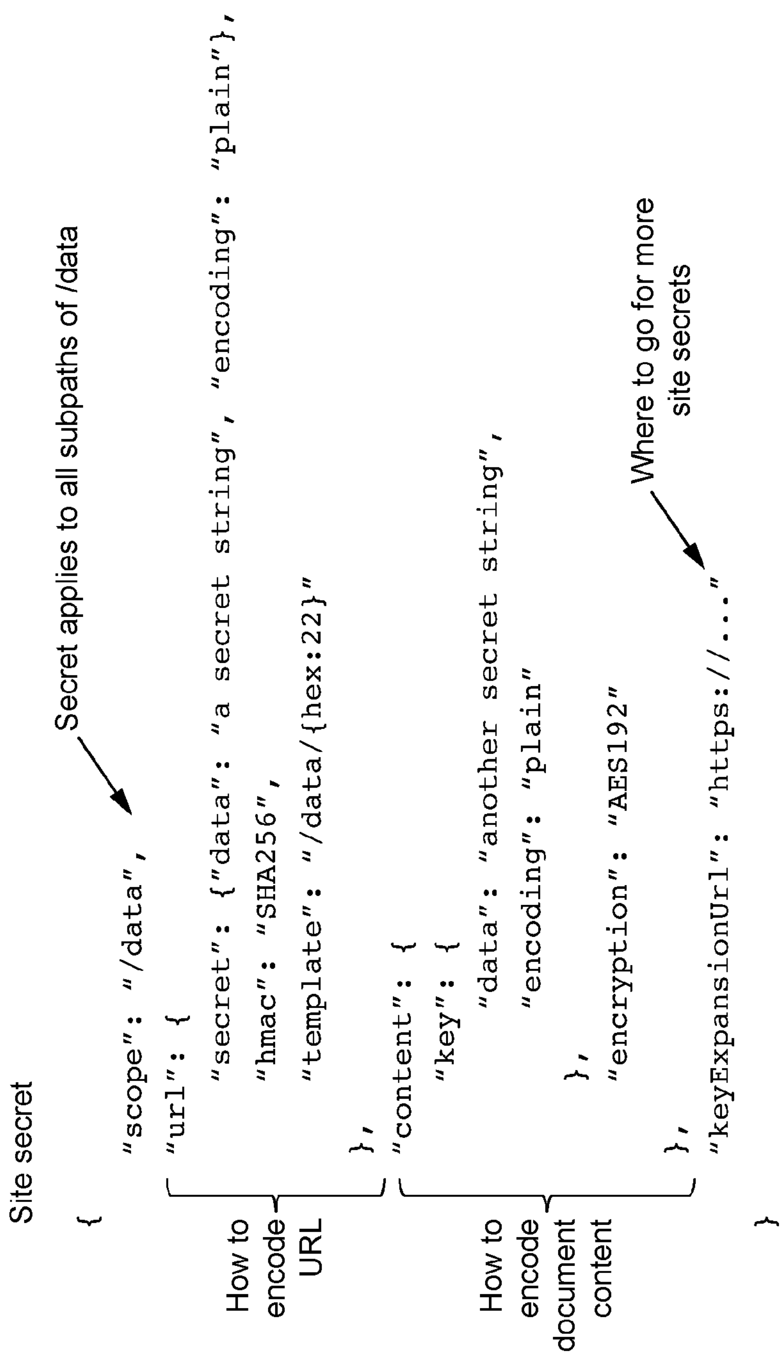

FIG. 2

METHODS OF ACCESSING AND PROVIDING ACCESS TO DATA SENT BETWEEN A REMOTE RESOURCE AND A DATA PROCESSING DEVICE

CROSS-REFERENCE TO RELATED APPLICATIONS

The present application is a National Phase entry of PCT Application No. PCT/GB2015/051564, filed on May 29, 2015, which claims priority to GB Patent Application No. 1409853.7, filed on Jun. 3, 2014, and also claims priority to GB Patent Application No. 1420101.6, filed on Nov. 12, 2014, which are hereby fully incorporated herein by reference.

The present technique relates to the field of data processing. More particularly, the technique relates to accessing, or providing access to, data sent between a remote resource and a data processing device.

Cloud computing services are becoming more common. More and more devices are being connected to the cloud, for example as part of the "Internet of Things". For example, relatively small devices such as temperature sensors, healthcare monitors and electronic door locks can be connected to the cloud so that they can be accessed and controlled using remote systems. For example, the door may be remotely opened from a remote platform, or data from a temperature sensor or healthcare monitor may be aggregated at a remote location and accessed from another device. Hence, there is an increasing amount of data being collected by cloud platforms and their providers.

However, there is also an increasing distrust of giving large companies such as the cloud provider data about an individual and the individual's devices. Currently, when data is provided to a cloud service then there is little protection for the user's personal information. Nevertheless, cloud services are useful and so it is still desired to be able to interact with other devices securely over the cloud. Such interactions should be efficient and minimize redundancy in the network so that data across the network can be accessed in the minimum amount of time. The present technique seeks to provide a more efficient access to data across a network within a secure environment.

Viewed from one aspect, the present technique provides a method of accessing data sent between a remote resource and a data processing device, the method comprising: caching data uploaded from the remote resource or caching data sent to the remote resource at one or more intermediate network nodes between the data processing device and the remote resource; and accessing the cached data stored at the one or more intermediate network nodes.

The present technique recognizes that caching data uploaded from the remote resource or caching data sent to the remote resource at one or more intermediate network nodes between the data processing device and the remote resource may occur before communicating the data to the data processing device.

The present technique recognizes that the cached data may be encrypted and that if the cached data stored at the remote resource is available at a plurality of network nodes, then the cached data may be obtained by the data processing device from one of the plurality of network nodes selected based on an expected transaction cost associated with obtaining the cached data from each network node. Moreover, if the remote resource can be accessed using a plurality of communication channels, then the data processing device may access the remote resource via one of the plurality of communication channels selected based on an expected transaction cost associated with each communication channel.

The present technique recognizes that there may be a need for proof of node ownership. Such a need may arise so that a device caching data to an intermediate node can verify or be verified that the device is the rightful owner of the intermediate node. For example, to avoid cache poisoning also known as domain name system poisoning, where an Internet address such as a URL may be replaced by that of another, rogue address, proof may be obtained from a cloud server that the data has been successfully stored in the cloud. On way to provide such proof is the sign the data with the origin cloud's secret key, so that all intermediate caches can infer that a URL was updated by the rightful owner. Since the cloud will only sign content uploaded by a valid user other intermediate caches only need to know the originating cloud's public key. The present technique also recognizes that when a device uploads data to a new intermediate node online then the device may retrieve a certificate from a target cloud server that contains an Access Control List (ACL) stating that the owner of the signed public certificate hash (usually the device's public) key is allowed to update that specific node. The ACL may further contain termination dates as well as what operations are allowed on given objects, source IP range restrictions etc. Should a device cache data upwards (i.e. caching data uploaded), the device may sign that node with the device's private key thereby allowing other devices to verify the signature with the device's public key. On demand, the device may present the device permission certificate generated during a brief online phase to the upwards caches. In this way, the present technique recognizes that upward caches can verify in a disconnected case that the device is the rightful owner of the intermediate node and can re-serve data downwards into the network. On demand downward devices may request a proof of ownership either directly from a target cloud or from an intermediate cache because the permission ACL is stored on the target cloud.

The method of the present technique may upload data from the remote resource or send data to the remote resource by signing the data with a secret key upon uploading or sending. In sending the data to the remote resource for instructing a specified operation to be performed using the remote resource, the data processing device may have or obtain authentication information for verifying that the data processing device has the right to instruct the specified operation to be performed using the remote resource. When accessing the cached data stored at the one or more intermediate network nodes the accessing may include the data processing device having or obtaining authentication information for verifying that the data processing device has the right to access the cached data. The authentication information may include a shared secret between the data processing device and the remote resource.

The method of the present technique recognizes that it is not just the data stored at remote resources that may contain personal or sensitive information. The URL (uniform resource locator) from which the resource is accessed may itself give away information. For example, a user may have a device whose URL includes information about the type, make, model, function or location of the device, or information about the user who owns the device. Similarly, a website may have a URL which may contain information describing or hinting at the interests or details of the person running the website. This means that often the information included in the URL of the remote resource may be as interesting to cloud providers or "big data" aggregators as the actual data of the remote resource. In current cloud platforms, the URL of the remote resource is open to all and visible to the cloud infrastructure (e.g. through requests sent to a server) and so potentially may lead to loss of private or sensitive information. To maintain privacy, it is possible to use a URL which does not give any meaningful information, such as a random string of characters, but this makes it harder for the resource to be accessed by both the person managing the resource and other users, since a random string of characters is difficult to remember.

The present technique further provides for a method wherein data is accessed between a remote resource and a data processing device by:

obtaining a first uniform resource locator (URL) corresponding to the remote resource;

obtaining secret data corresponding to the first URL; generating an obscured URL at the data processing device using the secret data corresponding to the first URL, wherein the obscured URL is for obtaining the actual location of the remote resource; and accessing the cached data from a remote resource at one or more intermediate network nodes using the obscured URL.

The first URL may be visible to the user of the data processing device and may not identify any actual location of a remote resource. The first URL may identify a location of a different remote resource to the remote resource accessed using the obscured URL. The obscured URL may be generated by performing a transformation of the first URL into the obscured URL using the secret data and the obscured URL may be generated based on the secret data corresponding to the first URL.

In a further aspect, the technique provides for a data processing device comprising:

processing circuitry configured to perform data processing; and communication circuitry configured to access a remote resource;

wherein the processing circuitry is configured to:

access cached data stored at one or more intermediate network nodes between the data processing device and remote resource, the cached data having been data uploaded from the remote resource or data sent to the remote resource.

In yet a further aspect the technique provides for an intermediate network node between a data processing device and remote resource comprising processing circuitry configured to perform data processing; communication circuitry configured to provide access between the data processing device and remote resource; and a memory store configured to store cached data;

wherein the processing circuitry is configured to cache data uploaded from the remote resource or cache data sent to the remote resource during communication between the data processing device and the remote resource.

The further aspect recognizes that the intermediate network node may be a gateway, network router or internet service provider device.

Aspects, features and advantages of the present technique will be apparent from the following examples which are to be read in conjunction with accompanying drawings.

FIG. 2 illustrates an example of a site secret for the remote resource;

Figure 1:
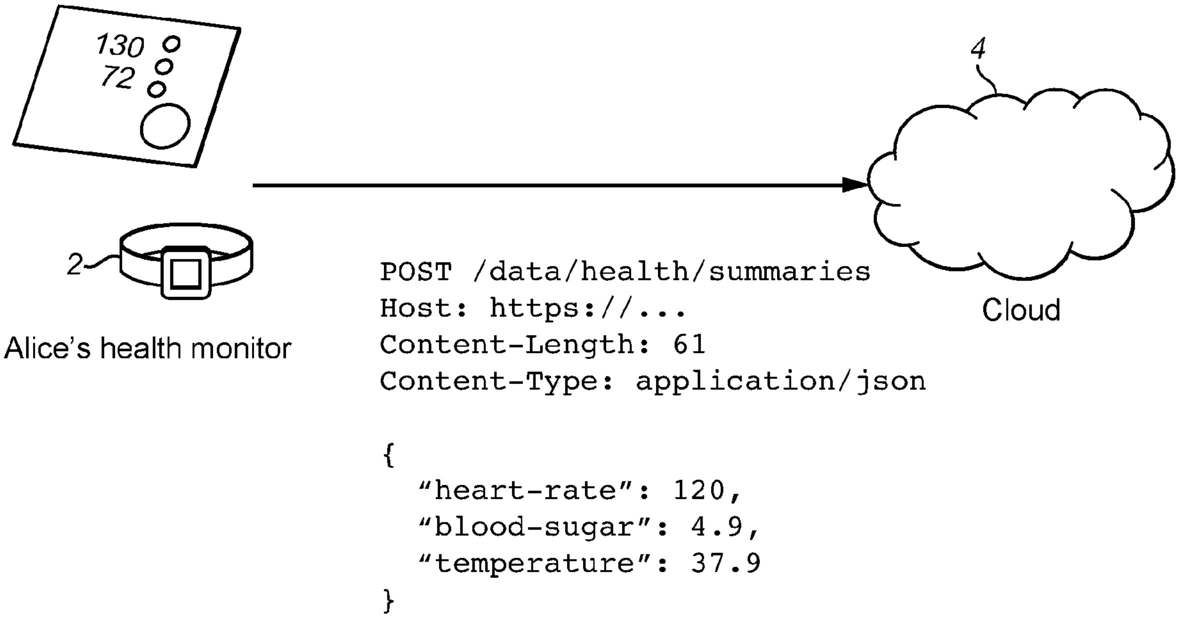
FIG. 1 illustrates an example of a data processing device accessing a remote resource.

FIG. 1 illustrates an example of a data processing device 2 accessing a remote resource 4 in the cloud when the present technique is not applied. For example, the data processing device 2 may be a health care monitor which monitors various parameters related to the user's health, such as heart rate, blood sugar level, temperature, etc. The monitored data is provided to a cloud service, such as a platform provided by a healthcare provider which can analyze the user's health data and flag health problems detected using the data. The data is posted to a remote location identified by a URL (e.g. /data/health/summaries). However, the URLs used by devices and users often contain intuitive information identifying the user, their device 2, or the purpose of the data, so that the URL can easily be remembered or understood by the user of the device 2. Therefore, the URL may often contain sensitive or personal information, such as the user's name or location, the device's make, model, type, or location, or information about the meaning of the data provided by the device. Therefore, the cloud provider, an internet infrastructure operator or other parties may be able to derive personal information from the URL even if the data stored at the URL is encrypted. There is an increasing distrust in allowing companies to access such information.

To address this issue, the data processing device may be provided with secret information as shown in FIG. 2. This secret information is collectively referred to as a "site secret". The site secret is provided for a particular URL ("first URL") and for a particular user or device. The user/device can use the first URL to identify the remote resource. However, the first URL does not identify the actual location of the remote resource. The site secret is for mapping the first URL to a different obscured URL which is used to find the actual location of the remote resource. In this way, there is no need for network operators or cloud providers to see an intuitive URL, as only the obscured URL needs to be exposed to the network. Nevertheless, the user can still use a nice intuitive URL to make interaction with the resource more convenient.

As shown in FIG. 2, the site secret includes a scope which specifies the remote resources to which the site secret applies. In this example, the scope portion indicates the paths or subpaths of the resources to which the site secret applies. In this example, the site secret applies to the path “/data”. Implicitly, the site secret may also apply to all subpaths of the path indicated in the scope. Hence, accesses to resources not within the specified path (including subpaths) may not succeed. In other examples, the scope may specify further conditions which must be met in order for an access to be successful (e.g. time based or use based conditions).

The site secret also includes URL encoding information which specifies how to generate the obscured URL of the resource. In this example, the URL encoding information includes a secret string to be used as a key for transforming the first URL into the obscured URL, data defining a transformation to use for generating an encoded string for the obscured URL (e.g. SHA256 in this example) and a template URL into which the encoded string can be inserted to form the obscured URL. SHA256 is a one-way transformation which means that even if the secret string (key) is known, it is not possible to use the key to transform the obscured URL back into the first URL. Other transformations may also be used (e.g. md5, other SHA algorithms, CRC32). In this example, the template is “/data/{hex:22}”, which means that a 22-character truncated string generated based on the SHA256 algorithm is inserted into the template to create the obscured URL. The string to be inserted into the template may be a truncated version of the actual result of the transformation (it is not essential to use all bits of the encoded string in the URL). In other examples the full string generated by the hash algorithm may be used.

The site secret also includes content encoding information defining how to encode document content or transactions to be sent to the remote resource. Another secret string may be used as a key for encoding the content, e.g. using the AES192 algorithm as shown in FIG. 2.

Figure 3:
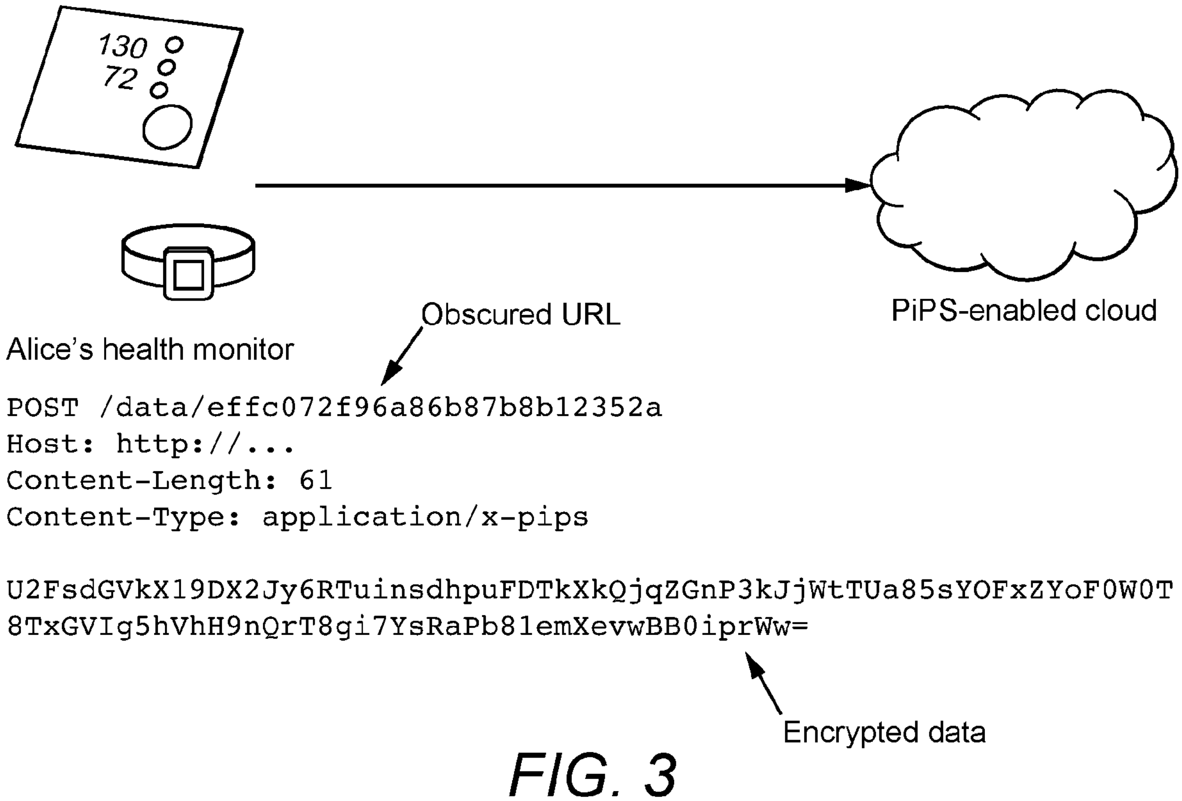
FIG. 3 illustrates an example of accessing the resource at an obscured URL generated using the site secret.

Hence, as shown in FIG. 3, instead of posting content in the clear to the first URL, the healthcare device 2 may post encrypted content to an obscured URL, so that both the content and the URL corresponds to an unintelligible string of characters which does not give away any sensitive information.

Figure 4:
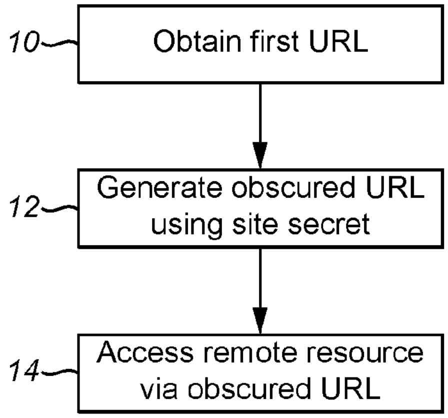
FIG. 4 illustrates a method of accessing a remote resource.

FIG. 4 illustrates a method of accessing a remote resource from a data processing device 2. At step 10, a first URL corresponding to the remote resource is obtained by the data processing device 2. The first URL may be obtained, for example, by the user typing in a URL into a browser, the user clicking a link in an email or website, reading a pre-stored URL, or accessing a fixed URL permanently embedded into the device at manufacture, or in any other way. At step 12, the site secret corresponding to the first URL is obtained, and used to generate an obscured URL. At step 14, the remote resource is accessed using the obscured URL. Hence, this approach allows devices to serve data and be accessed remotely without giving away information in the URL of the device.

The data processing device 2 may be any processing device which needs to access a remote resource. The present technique is particularly useful for small scale devices such as sensors, controllers or wireless nodes in the cloud. In some cases, the data associated with the remote resource may be served from the resource itself such as a temperature sensor, or healthcare device. In this case the device itself may be identified by the obscured URL. Alternatively, such resources may be given a cloud address for high availability which is then accessed from a separate server corresponding to the resource device.

For privacy, it is preferable that the first URL does not correspond to any real location within the cloud. This means that the first URL is completely invisible to network operators and cloud providers. However, in some cases the first URL may also map to a real location on the network, for example when converting a legacy site to a new site as discussed below with respect to FIGS. 10A to 10D. Also, in some cases the first URL may identify a location with different content to the remote resource identified using the obscured URL.

FIGS. 2 and 3 show an example in which the obscured URL is generated by transforming the first URL using a transformation algorithm such as SHA256. However, it is also possible to generate the obscured URL in other ways. For example, rather than providing a separate site secret including a key for scrambling the URL, the secret data may instead be included in the first URL, with different users provided with different secret data. For example, a first URL http://meriac.com/pips/this/is/my/tv?secret=4567 may include secret data 4567 for a particular user or group of users. The device 2 may hash this URL using a predetermined algorithm (e.g. CRC32 or SHA256) to generate a secret string “9677BE35” so that the obscured URL becomes http://meriac.com/pips/9677BE35. In general, the secret data may be any data which provides information for generating the obscured URL which should be accessed instead of the first URL.

In some cases, a third party plugin or website-frame work may be used to generate the obscured URL. For example, a Party A may create a plugin that hashes URLs into node IDs (obscured URLs). The plugin does not understand the concept of having a URL secret, but can decrypt and verify URL file payloads. Another Party B may provide a Website-Frame work that contains a java-script-include on each page that takes a pre-defined URL-parameter (let’s call it “secret”) and rewrites dynamically URLs of subsequent page requests of images and other content linked on the page. Another Party C (e.g. a content author) publishes a link to http://C.com/site.html?secret=xyz to a user D and a link http://C.com/site.html?secret=abc to a user E (plus individual keys K(D) and K(E)), and authors user-specific key nodes (see below) for the individually personalized URLs. Hence, in this example the secret data for each user is included in the first URL itself.

The user D of the end device 2 then visits site C, and the plugin A performs secret-less hashing of http://C.com/site.html?secret=xyz into http://C.com/45c2d52c8b514a01. The plugin A performs decryption of fetched content from this URL using K(D). The user’s browser executes the embedded JavaScript framework in site C, which rewrites all URLs in the page by appending the secret=xyz parameter. Pages or resources fetched by the browser are then intercepted by the browser plugin A and hashed without additional secrets. For user E, the process may be similar to user D, but with a different entry link.

It is possible to provide site secrets which can be used for multiple different remote resources. For example, a particular party may provide a site secret which can be used by a user to access resources from a range of locations managed by that party. Hence, one secret may cover a whole range of URLs, and when encountering a new URL, the data processing device may already be in possession of a secret suitable for use with that URL and so may not need to acquire a new site secret.

The obscured URL may be obtained by the device 2 in different ways. For example, the generation of the obscured URL may be implemented using embedded functionality within the device, using code which is part of a browser or other software executed by the device 2, or using a browser plugin, applet or javascript obtained from a third party.

It is possible for the obscured URL generated using the first URL to identify the location of the remote resource itself. However, it may be desirable to provide different users with different versions of content or access to different resources. To maintain security and the ability to individually control the access to different users, it can be useful to provide each user with a different site secret mapping to a different obscured URL. However, if each obscured URL actually contained the remote resource itself, it would be difficult and time consuming to maintain many different copies of the same remote resource for each user at different URLs.

Figure 5:
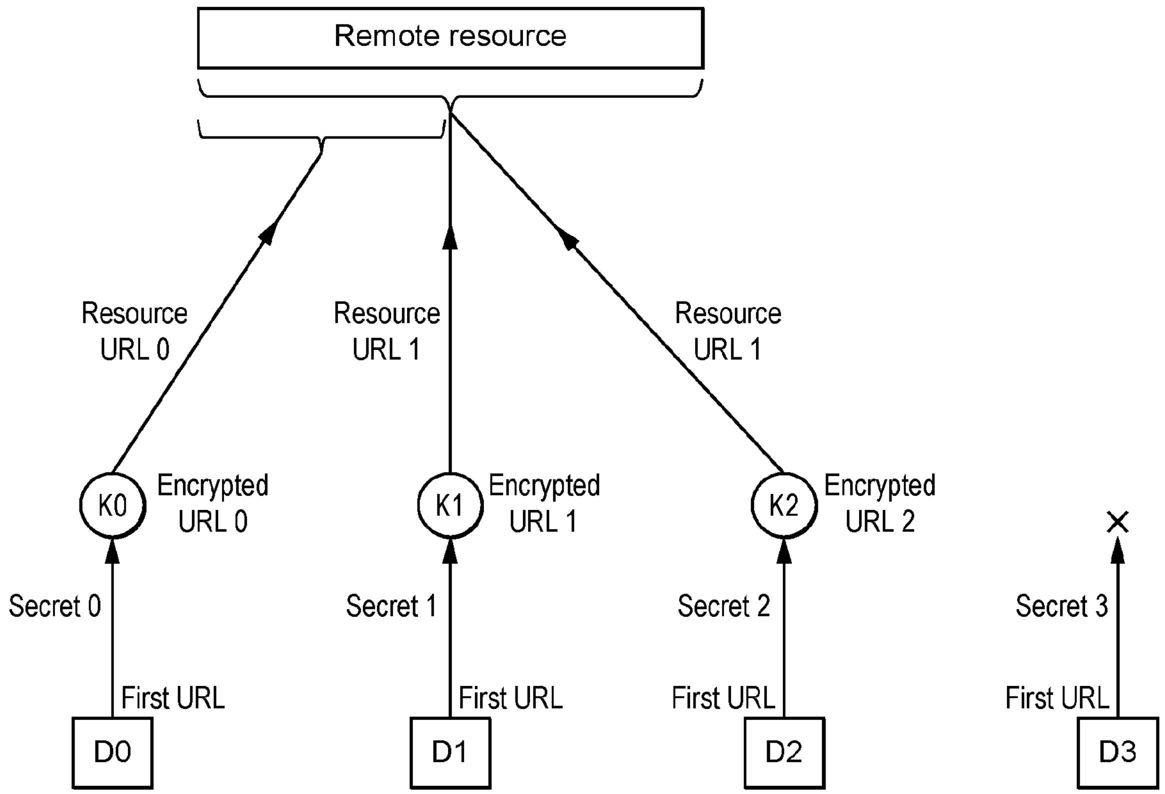
FIG. 5 shows an example where the obscured URL identifies a key node resource which contains data for providing the URL of the remote resource.

FIG. 5 shows how different representations of the same resource can be managed more efficiently using key node resources. As shown in FIG. 5, the obscured (encrypted) URL generated using the site secret for a given device may identify the location of a key node resource K0-K2 which does not store the actual remote resource. Each key node resource K0-K2 contains data for obtaining the actual resource URL of the remote resource. This means that different users can be provided with access to different parts of the remote resource by specifying different resource URLs at the key nodes (or by specifying the same resource URL but with different pieces of associated information identifying which parts of the URL are accessible). For example, in FIG. 5 the users of devices D1 and D2 access key nodes K1 and K2 respectively to obtain resource URL 1 (e.g. http://abc.com/data/18659458.php) which gives them access to the entire remote resource. However, a user of device D0 obtains resource URL 0 from key node K0 (e.g. http://abc.com/data/58159873.php) which only allows them to access a subset of the remote resource. Hence, the different resource URLs provided by each key node may correspond to overlapping parts or subsets of the remote resource. In other examples the resource URLs provided by different key nodes may correspond to different remote resources entirely.

This approach allows different representations of the data to be provided to different users. For example, the different representations provided for the remote resource may provide different types of content, different content quality (e.g. full images or compressed images), different granularity of access to content (e.g. time series data sampled at hourly increments or daily increments), or different subsets of data available to users. Each user may use the same first URL, and so may not be aware that other users have different access to data or that there are multiple representations of data being provided by the remote resource. The access to the different forms of the resource is controlled by providing different site secrets for each user, which cause the first URL to be mapped to different obscured URLs.

The key nodes K0-K2 may also store data for decrypting content at the resource URL. This means that only authorized users who have successfully located a key node for the resource can obtain the decryption key for decrypting the content.

The use of key nodes K0 to K2 as shown in FIG. 5 is also useful since different users can be granted and/or revoked access to the remote resource by simply manipulating the key node resources without modifying the remote resource in any way.

Figure 6:
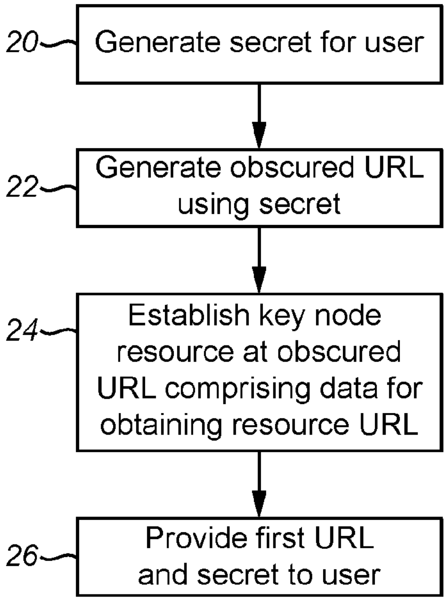
FIG. 6 illustrates a method of providing a data processing device with access to a remote resource.

For example, FIG. 6 shows a method of providing a user of a data processing device 2 with access to the remote resource. The method can be performed by a data processing apparatus for a content author or party managing the remote resource. At step 20, a new site secret is generated for the user to be granted access to the remote resource. At step 22, the user's secret is used to generate the obscured URL for that user (the obscured URL may be generated in the same way as at step 12 of FIG. 4). At step 24, a key node resource is established at the obscured URL, including data for obtaining the resource URL of the remote resource. At step 26, the first URL which the user will use to identify the resource, and the site secret corresponding to the first URL, are provided to the user's data processing device. The user's device can then access the remote resource using the method of FIG. 4 via the key node resource as shown in FIG. 5.

Access to the remote resource by a particular user can be revoked by removing the key node resource at the URL generated using the site secret for that user. For example, see device D3 of FIG. 5 which has its access revoked by removing the corresponding key node resource. When the key node resource is removed, the user of the device can no longer access the remote resource since there is no way for them to obtain the resource URL. Hence, there is no need to move the actual resource when a user's access is revoked. For added security the resource could also be moved, in case a user has managed to obtain and store the resource URL.

Figure 7:
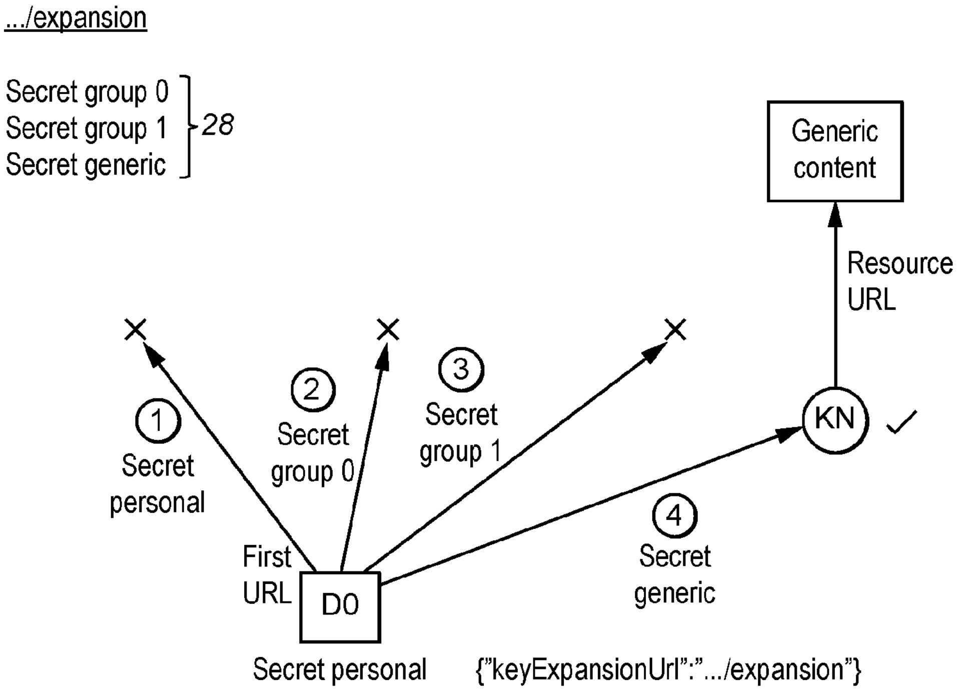
FIG. 7 illustrates an example of using an expansion URL to obtain different site secrets for accessing the resource.

A user may have access to different site secrets for the same remote resource. For example, a user may have a personal site secret but may also have access to a group site secret associated with a group of users or a generic site secret which is available to everybody. The expansion URL shown in FIG. 2 may be used to obtain additional site secrets. As shown in FIG. 7, a number of site secrets 28 may be stored at the expansion URL. The data processing device D0 may obtain the site secrets from the expansion URL, in addition to the initial site secret held by the device D0. The device D0 then attempts to access one or more obscured URLs generated using the different site secrets until an access is successful. For example, the device D0 may try each obscured URL in turn. In the example of FIG. 7 the device first tries the obscured URL generated using the personal secret, then tries obscured URLs for two different group secrets, before finding that the obscured URL generated using the generic secret successfully locates a real location KN on the network from which the resource URL can be obtained. The device D0 may also try multiple accesses in parallel in case one fails, to speed up the access. If multiple accesses are successful, there may be a predetermined priority order which determines which access to follow up on. This approach is useful because it means that group secrets do not need to be held permanently by end devices D0, and instead can be controlled more carefully from the expansion URL.

Figure 8:
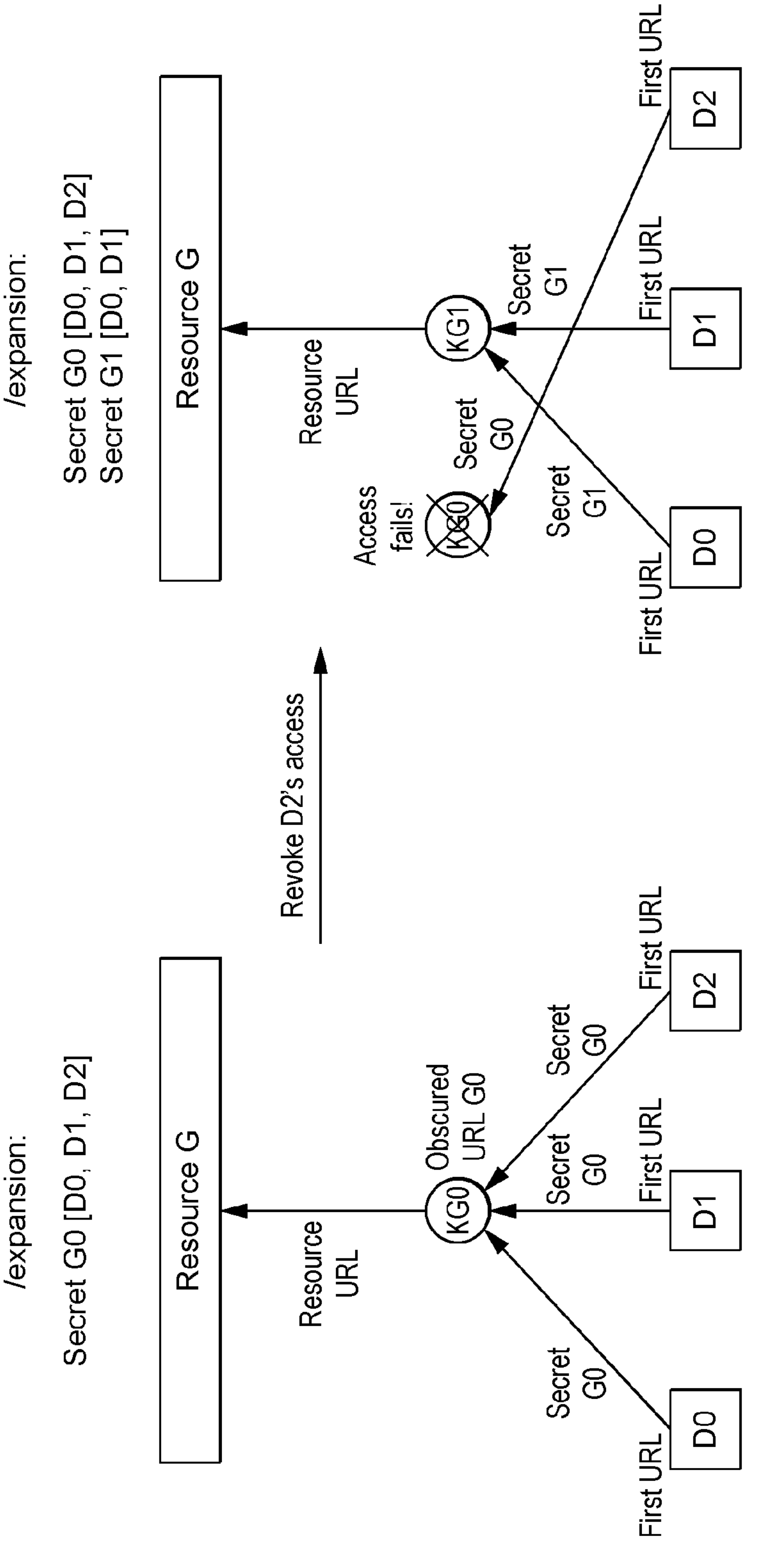
FIG. 8 shows an example of revoking a user's membership of a group allowed to access a remote resource.

FIG. 8 shows an example of a revoking access to a remote resource for a selected user within a group previously allowed to access the resource. As shown in the left hand part of FIG. 8, the expansion URL includes a group secret G0 for a group of users of devices D0-D2. The group secret G0 is used to generate an obscured URL G0 of a key node KG0 from which the resource URL of the shared resource can be obtained. This allows the devices D0-D2 to interact with the resource.

However, the user of device D2 then leaves the group and so D2's access to the remote resource is to be revoked. For example, the resource G may be a device for controlling a door lock and the user of device D2 may have left the organization who owns the door, and needs to be prevented from entering. To achieve this, a new site secret G1 is generated at the expansion URL for a new group G1 of users D0, D1 which excludes the revoked user D2. Hence, when the devices D0, D1 access the expansion URL they obtain both secrets G0, G1 while device D2 only obtains secret G0. A new key node KG1 is created at the obscured URL corresponding to the new site secret G1. The key node KG1 again has the resource URL identifying the resource. The original key node for this group KG0 is then removed so that any access to the URL obtained using secret key G0 will fail. Hence, when devices D0 or D1 access the first URL, the secret G1 successfully maps to the obscured URL of key node KG1 and so they can still access the door to unlock it. However, device D2 only has secret G0 which no longer maps to a real location, and so cannot locate the resource anymore. Hence, this mechanism using key nodes and the expansion URLs provides an efficient way for controlling access to resources without having to republish the resource itself.

Figure 9:
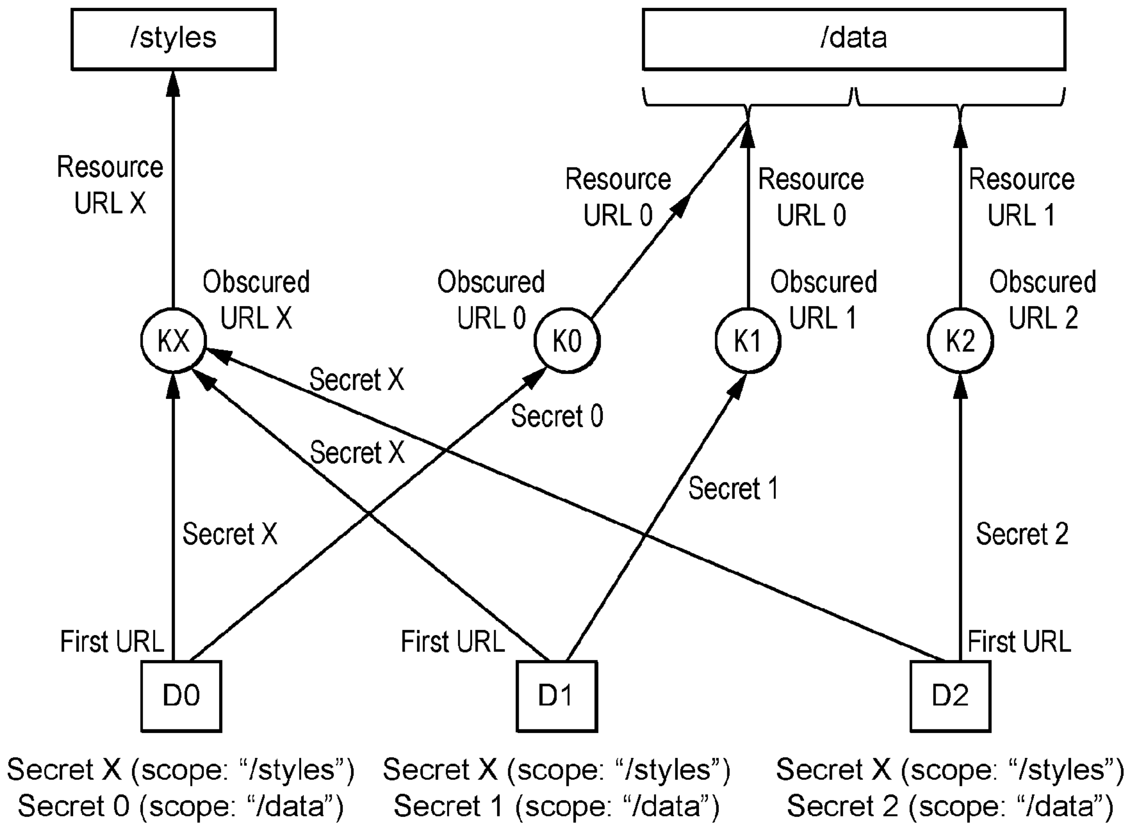
FIG. 9 shows an example of providing different site secrets for accessing different resources corresponding to parts of the same site or collection of resources.

As shown in FIG. 9, it is possible to provide different site secrets corresponding to different resources within a same site or same collection of resources. For example, users may generally be allowed to access the style sheets (CSS files) of a website, but individual access rights may be controlled for the data of the website. The scope parameter shown in FIG. 2 may be used to select the parts to which the secret applies. Hence, a first generic secret X can be provided with scope "/styles" for accessing the style sheets for the website. Individual secrets may then be provided for scope "/data" which allow each device D0-D2 to individually access different subsets of the data. The scope "/styles" for secret X means that this secret cannot be used to gain access to the "/data" portion of the website.

Figure 10A:
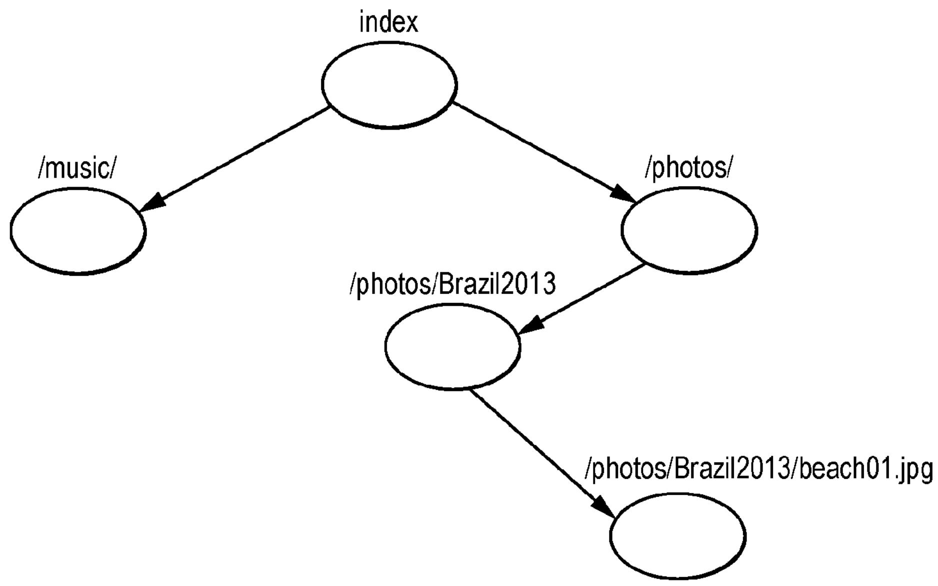
FIGS. 10A to 10D illustrate a method of transitioning a legacy resource to a more secure resource using obscured URLs.
Figure 10B:
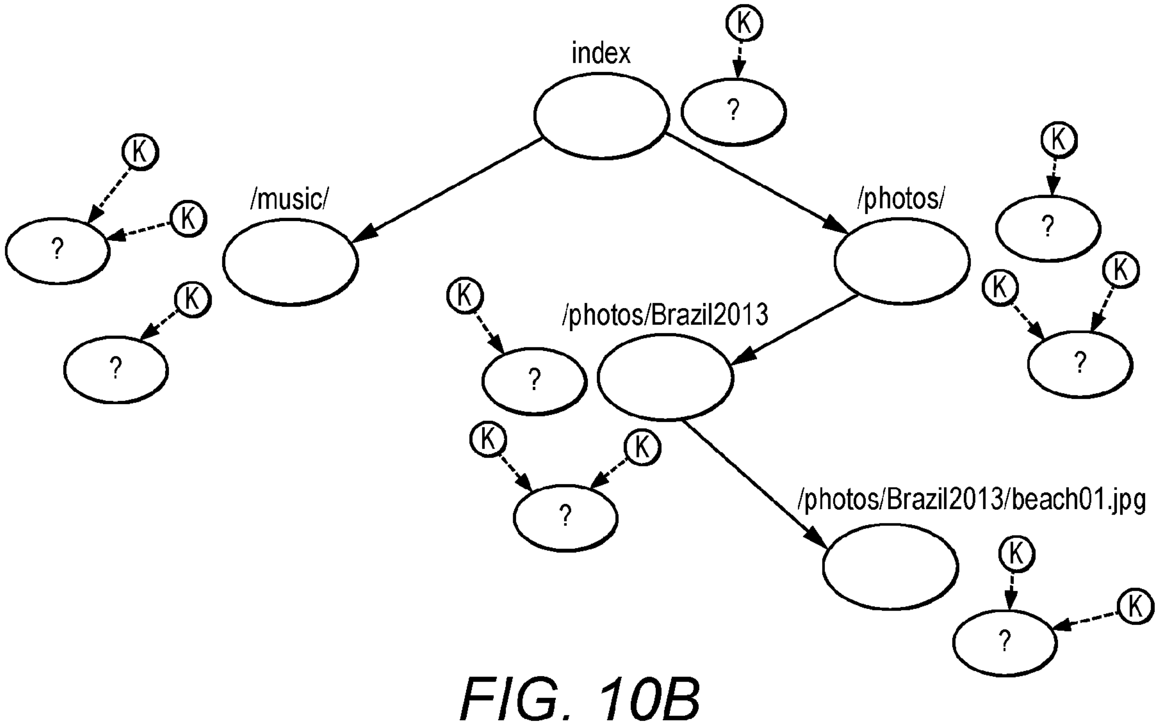
Figure 10C:
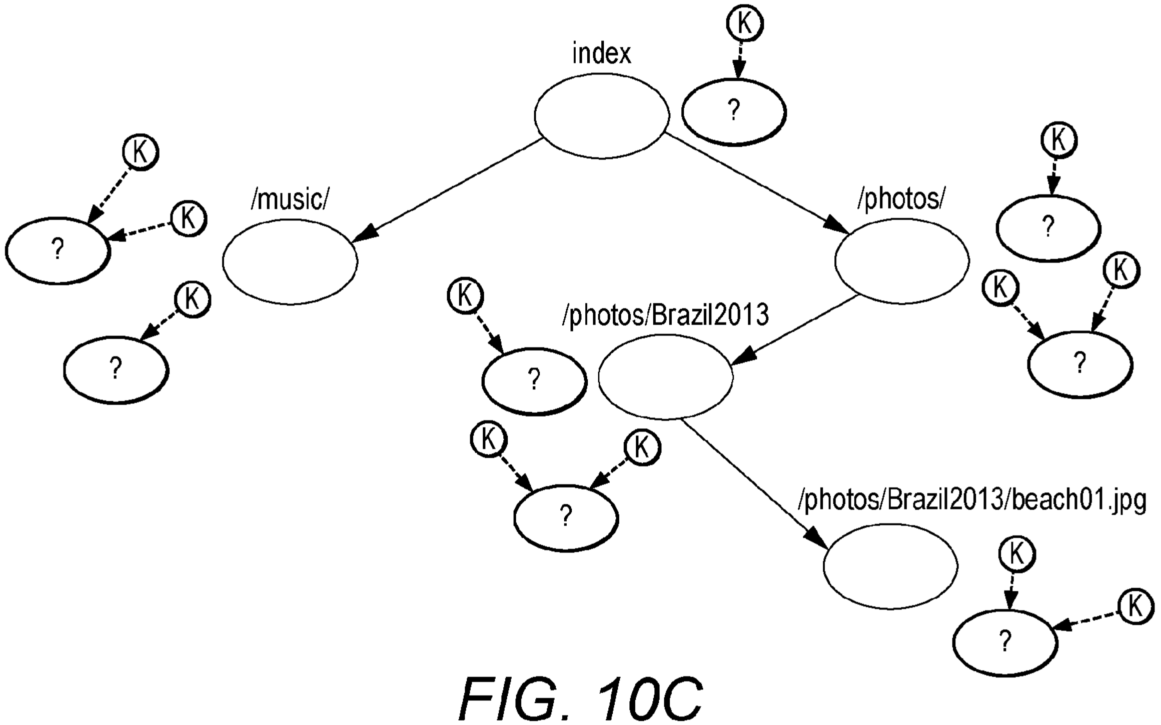
Figure 10D:
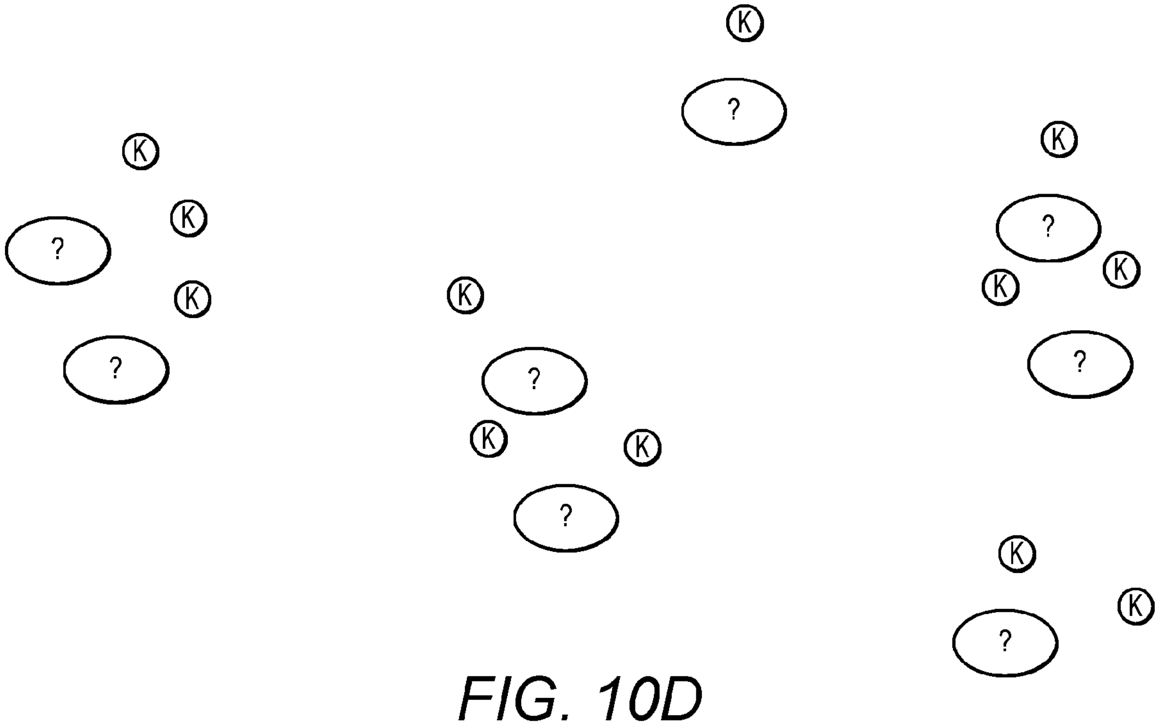

As mentioned above, the first URL (intuitive URL) may not correspond to any real location within the network to prevent cloud operators gaining access to sensitive information. However, legacy sites and devices may already be published on the cloud using such an intelligible URL. In this case, the legacy site may be transitioned to a more secure site using the present technique as shown in FIGS. 10A to 10D. In FIG. 10A, the legacy site is shown with intelligible file paths and file names. In FIG. 10B, a new site is created in which the data from the legacy site is replicated at non-intelligible resource URLs (indicated by the question marks in FIG. 10B). Also, key node resources K are established for users of the website. The key node resources K have obscured URLs generated using the site secret for the user or group or user, and contain data identifying the corresponding resource URL. For a time, the legacy site and the new site can run in parallel, so at this time the first URL for the new site may still map to a real location on the network corresponding to the legacy site. Once enough users have access to the new site, the legacy site may be deactivated as shown in the faded lines of FIG. 10C, leaving only the private site whose URLs are unintelligible. As shown in FIG. 10D, the server's view of the website is then completely anonymous since all URLs used for the site are obscured URLs.

Figure 11:
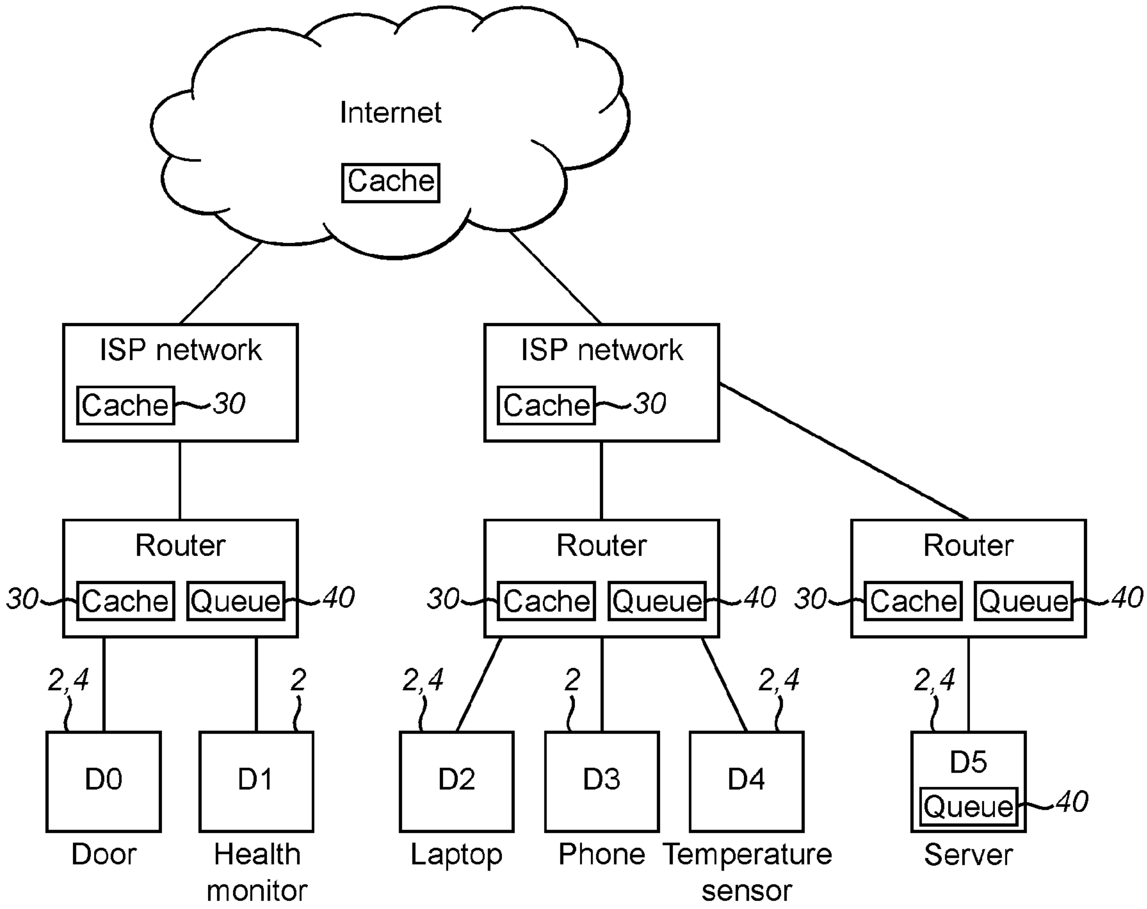
FIG. 11 shows an example of a network in which data and transactions for remote locations may be cached at nodes of the network.

As shown in FIG. 11, the data processing device 2 may correspond to various devices such as a laptop or other computer D2, mobile phone D3, server D5, temperature sensor D4, health monitor D1 or door control unit D0 for example. Similarly, the remote resources may correspond to similar devices D0-D5. As indicated in FIG. 11, some devices D0, D2, D4, D5 may function both as a remote resource 4 to be accessed by other devices and as a data processing device 2 for accessing remote resources. The devices communicate with each other via the Internet (cloud), using various intermediate network nodes such as network routers and ISP (internet service provider) devices and networks. It will be appreciated that the network diagram in FIG. 11 is schematic and that there are many different ways of implementing the network.

Since the URLs of remote resources are anonymous using the present technique, and also the transactions and data exchanged by devices may be encrypted, then there is no danger of leakage of information to the network. This allows intermediate network nodes, such as a router or ISP network device, to have a cache 30 for caching data or transactions exchanged with a remote location, without any security or privacy risk. For example, when the health monitor device D1 uploads data to the server D5 then the posted data can be cached as it passes up the network.

By caching the data at different points within the network, this means that if the data needs to be accessed by the device D1 then it can be obtained more quickly from a cache 30 in the home router or the ISP network than if it had to go all the way back to the server D5. Similarly, transactions for triggering devices to perform actions may be stored in a queue 40 within the device D5 initiating the transaction, or within another network node. For example, if the user of the laptop D2 or phone D3 wishes to open the door associated with device D0 (e.g. to let a friend or neighbor into their house), then the laptop of phone may issue a transaction to the door device D0 to open the door. However, the door device D0 may not be active at this time, e.g. it may be in a power saving mode and may only wake up periodically to check the queue 40 for transactions. When the door device next wakes up, it can poll the queue 40 and then open the door. The transactions in the queue 40 may be encrypted. By providing a queue 40 in the end device D5 or intermediate node of the network, the phone or laptop D2, D3 and the door D0 can communicate asynchronously so that it is not necessary for both devices to be active simultaneously in order for them to communicate.

Figure 12:
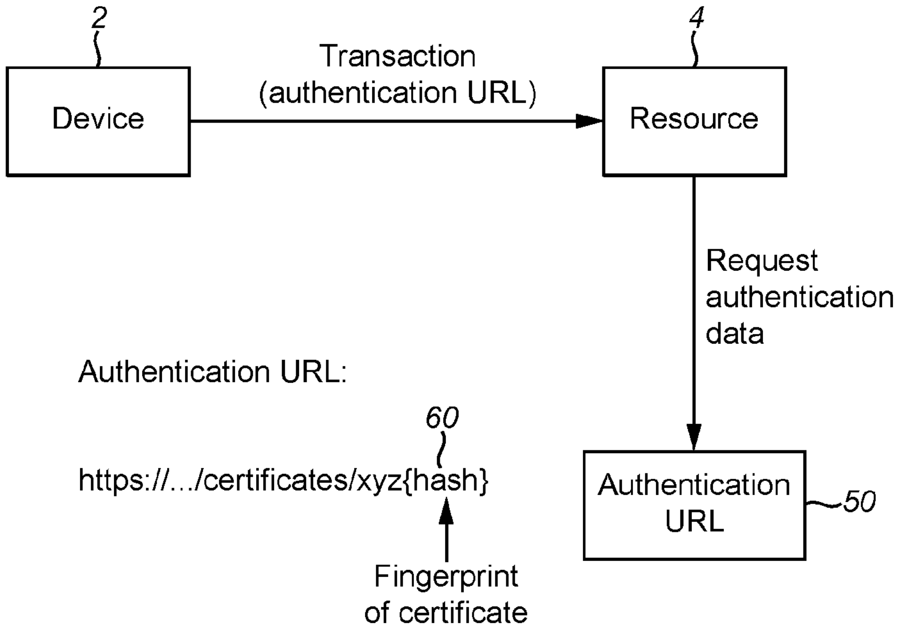
FIG. 12 shows an example of obtaining authentication information for verifying that a device is authorized to instruct an action to be performed at the remote resource.

In order to read or write data from a remote resource or perform an action using the remote resource, it may be necessary for the device issuing the transaction to prove its identity and verify that it is allowed to take this action. Hence, as shown in FIG. 12 when the device 2 issues a transaction for a device 4 associated with the remote resource, the device 2 may specify an authentication URL identifying a location 50 from which the device 4 associated with the remote resource can obtain authentication data for the device 2. For example, the authentication information may include certificates and public keys which verify the device's identity. In some cases there may be a chain of certificates where different parties authenticate different sub-parties to provide further authentication and so the identity of the end device 2 may need to be verified using several certificates. It is also possible for the device 2 to provide the authentication information directly to the resource 4 as part of the transaction. However, especially if the device 2 is a relatively small device such as a sensor, then it may be more convenient for the authentication information to be obtained from the authentication URL 50. When obtaining the authentication information from the authentication URL, the remote device 4 need not obtain the authentication information using the same communication channel or route that was used to send the transaction from the device 2. For example, when opening a door by submitting a transaction over Bluetooth, the door may use a different route (e.g. using a house router or wired connection) to fetch credentials from the authentication URL.

The authentication URL provided with the transaction may include a fingerprint portion 60 which is generated using the authentication information for the device 2. For example, the fingerprint portion 60 may be a hash of part of the certificate or public key of the authentication information. This means that to be able to direct the resource device 4 to access the authentication information from the authentication URL, the device 2 sending the transaction must itself have access to the authentication information. This improves the security of the system by reducing the chance that an unauthorized device could somehow direct the resource device 4 to a valid authentication URL with valid authentication information.

The authentication information may be cached at various locations within the network to make it quicker to access the authentication information from a local network node. The authentication information may define which particular actions can validly be carried out by the remote resource when instructed by the device 2. The authentication information may also specify validity information indicating a period of validity for the authentication information (e.g. an expiry date/time, a period with a start data/time and end date/time, or a non-continuous period). It can be useful for the authentication information to separately define a period within which the authentication information is valid and a period within which the authentication can cached by network nodes. Even if the authentication information is valid for a relatively long period, the cacheability period may be set to a shorter period. For example, a particular certificate may be valid for six months so that the authenticator does not need to update the certificates very often. However, by only caching the certificate for a shorter period (e.g. one day), access to a given remote resource can be revoked more quickly since cached copies of the authentication information will be discarded at the end of the day and then the certificate would need to be obtained again from its original source in order to continue access, allowing access to be controlled more easily.

A summary of some features and advantages of the present technique, known as "PiPS" (Privacy in Plain Sight), is provided below.

Goals:
- A PiPS-enabled web service may:
- Maintain privacy—users control who accesses their data (including cloud services)
- Provide personalized information for different people/groups
- Minimize workload for low-power devices, moving it to cloud-services instead
- Enable caching, lowering network requirements and improving performance
- Support asynchronous operations, to work with limited-connectivity devices
- Support time-series data Principles:
- Publish from the device, serve from the cloud
  - A device might make some resources/data available, but might only wake up and connect to the wider web occasionally.
  - In this case, having a cloud service (including "mini-clouds" such as local routers) host or mirror the data means high availability, while still allowing devices to be lower-power.
- Safely use untrusted data-stores/mirrors/caches
  - With PiPS, you have control over who understands your data, regardless of where it is stored. Data is stored encrypted, at obfuscated URLs—only devices and people who have permission to read the data will be able to understand it.
  - This means that you don't have to trust every data-store, mirror or caching proxy that sees your data. You can allow anybody to proxy/cache your data (for high availability) without privacy concerns.
- Asynchronous communications across untrusted intermediaries
  - With PiPS, interaction with devices is asynchronous. Actions intended for the device can be queued up in proxies or cloud services, waiting for when the device is next online.
  - These actions are also stored encrypted, meaning that device-to-device communication can be private (even if both devices are only occasionally online), without exposing the communications to a central service.

Broad-strokes design:
- Surrogate URLs and encrypted content
  - Resources have nice friendly URLs ("conceptual URLs"), so published content and interactions can be organized in a nice way.
  - However, the URL that is actually requested from the server is different: an opaque URL that does not reveal the nature of the information to the server, proxies, caches, etc.
  - All content is stored in encrypted form, so only the end-devices can understand it.
- Perform actions using Queues
  - A PiPS Queue is a list of pending actions/notifications. To perform an action, you POST it to a Queue. The target device then pulls actions off the Queue to execute them.
  - Queues can be monitored in different ways—so a highly-connected device can maintain an open connection to the cloud to get instant notifications, a less-connected device could poll once a minute, etc.
  - If an action requires a response, then a "response Queue" can be included, to which the results of the action can be sent.
- Time-series data in Queues
  - A Queue can be "turned around"—instead of many people adding actions to a queue and one device reading it, you can have one device publishing events to a queue, and many people reading it.
  - The methods for monitoring queues remain the same (polling, notifications, WebSockets, etc.). Since the content is encrypted, Queues can be proxied/cached—so the original Queue might only support polling, but proxies can layer WebSockets on top of that.
  - This means that a device can publish a set of events (using a simple POST), and delegate the complex queries (e.g. "all events since . . . ") to cloud services, proxies, et cetera.
- Site secrets and personalized content
  - A "site secret" is the information required to translate a resource's "conceptual URL" into a surrogate URL, and to decrypt the content.
  - Different people are provided with different secrets—so they will end up at different surrogate URLs, so they can be provided with different versions of the content.
- General principles:
- Not trusting cloud providers
  - Don't leak data, structure, anything
- Static resources (mirrorable/proxy/offline cache)
  - Devices can publish as many as they like
  - Supply custom content for some people
- Actions submitted to queues
  - Authentication by certificate chain
- Fits into existing web Not trusting cloud providers: There's an increasing distrust of giving large companies data about yourself. Our current protection (mutable, rarely-read terms of service) is basically just trusting a company to behave well. However, cloud services are useful, especially for devices with lower network availability, so we still want them.

Data control: How about we never give the cloud provider usable data in the first place? Encrypt everything, Uninformative URLs. This also gives us no fear of mirrors/proxies.

Comparison:

The data itself

Bad: plaintext data readable by anyone (inc. cloud)

Good: opaque blobs

Requests made to server

Bad: https://cloud.iot/my-house/bedroom/marital-aids/ . . .

Good: https://cloud.iot/c2V4bWFzdGVyLTMwMDA

Devices publish resources: We give all devices the ability to publish resources. These resources could be served from the device itself when available (e.g. coap://<ipv6-address>/a210Y2h1bi1rZXR0bGU), with users relying on various caches when it is not. Alternatively, these resources could be given a cloud address (e.g. https://iot.arm.com/a210Y2h1bi1rZXR0bGU) for high availability. Requires agreement with cloud, but easier for device (generated only once, always served from cloud). Note that a resource has only one URL—the above two URLs are not equivalent.

Verifiable Owner: The URL for each resource can contain a part computed from the fingerprint of the certificate to guarantee integrity even when served from untrusted sources.

Surrogate Resources: Customizing content and enabling privacy.

Say the client has a secret comprising three parts:

Scope: http://me.example.com/iot/geraint

Template: http://me.example.com/iot/{hmac}

Secret: site-secret

When accessing a resource in this scope, the client actually accesses a different URL to the one it is given.

1. HMAC(original-url, secret)
2. base64url(hmac)
3. Use inside template

Example: With the above secret, when accessing the resource http://me.example.com/iot/geraint/temp:

1. HMAC (http://me.example.com/iot/geraint/temp, site-secret)
2. base64url: d2hhdGV2ZXI
3. Fill template: http://me.example.com/iot/d2hhdGV2ZXI The server only sees http://me.example.com/iot/d2hhdGV2ZXI—nothing that hints to the conceptual structure of the site.

The original URL MAY still resolve to a plain-text resource, to give something useful/informative to clients not using this scheme. But this is not essential.

Key nodes: Duplicating content is generally inefficient. The actual node at the calculated URL could be a "key node", meaning that it contains the URL of the actual content along with a decryption key—all encrypted using the site secret used to calculate that URL.

Privacy-enabled Mode: Private versions of resources and plain resources do not mix. If you are viewing a private version of a resource (hopefully with some visual indication), then your clients should not follow links or fetch related resources with their original URL. If the surrogate resource 404*s*, then the request should fail. This means that the "original resource" for hidden resources doesn't need to actually exist, and shouldn't be requested, keeping the actual structure of the resources hidden from the server.

Multiple secrets: Even using key nodes, it is a burden to calculate a surrogate node for every possible user, for every resource in your site. However, a user can be in possession of multiple site secrets, such as a personal site secret and group site secret. This way, content that is available for every member of a group can use a single surrogate node, while other content can be encoded on a person-by-person basis.

Obtaining More Secrets: In reality, you don't want to hand the group site secret out. Otherwise, when you change it (e.g. to exclude a group member) you need to re-distribute the new one to everyone. Instead, you only hand out personal site secrets. To obtain more site secrets, clients can fetch the "scope" URL (using their personal site secret). The resulting document will be a list of site secrets to use for subsequent browsing.

Alternative: have separate "secret expansion" URL, instead of using scope

Website sections: Not only can you provide additional site secrets for group content, you can provide secrets for only parts of a site. For instance, if all your JavaScript and CSS lives in /style/, then you can specify a site secret specifically for that section. That way, clients do not waste effort first trying to access those resources using personal and group site secrets.

Action Queues: Instead of taking actions directly, resources can specify a queue to which actions can be posted. There can be more than one of these queues, listed in preferential order—e.g. first the direct one (usable by BlueTooth locally), next hosted by local WiFi router, then on cloud service. Resources describe the actions that can be taken using their queues, optionally with an encryption key so that such the actual actions remain opaque to the cloud service.

Authentication by Certificate Chain: When an action is submitted, the URL of a resource (certificate) can be supplied that explains why the agent believes it has permission to perform that action. Each certificate specifies a public key that can be used for a particular purpose, and comprises:

Validity conditions (time/location/whatever)

Constraints (e.g. "Can turn on")

Possibly reference to parent certificate

Understanding Certificates: The actual vocabulary of what actions are/aren't allowed doesn't need to be universal—just understood by the end device. There may be some standard ones, though, e.g. Ownership—can do anything, Full use—can do anything except change owners Example:

For the private key: <ABCDE>

Until: 2014-06-18T18:32

Allowed actions:

view recent history issue new certificates like:

Allowed actions:

view recent history

This certificate could be used to let <ABCDE> view recent history.

It could also be referenced by a new certificate (signed by <ABCDE>) authorizing another entity to view the recent history.

Offline case (e.g. unlocking a door in the desert)

If wider network access is not available, then the agent wishing to perform the action can make itself available as a mini-cloud/-proxy, therefore making the certificate chain available as well.

Viewed from one aspect, the present technique provides a method of accessing a remote resource from a data processing device, the method comprising:

obtaining a first uniform resource locator (URL) corresponding to the remote resource;

obtaining secret data corresponding to the first URL;

generating an obscured URL at the data processing device using the secret data corresponding to the first URL, wherein the obscured URL is for obtaining the actual location of the remote resource; and accessing the remote resource using the obscured URL.

The present technique recognizes that it is not just the data stored at remote resources that may contain personal or sensitive information. The URL (uniform resource locator) from which the resource is accessed may itself give away information. For example, a user may have a device whose URL includes information about the type, make, model, function or location of the device, or information about the user who owns the device. Similarly, a website may have a URL which may contain information describing or hinting at the interests or details of the person running the website. This means that often the information included in the URL of the remote resource may be as interesting to cloud providers or "big data" aggregators as the actual data of the remote resource. In current cloud platforms, the URL of the remote resource is open to all and visible to the cloud infrastructure (e.g. through requests sent to a server) and so potentially may lead to loss of private or sensitive information. To maintain privacy, it is possible to use a URL which does not give any meaningful information, such as a random string of characters, but this makes it harder for the resource to be accessed by both the person managing the resource and other users, since a random string of characters is difficult to remember.

The method of the present technique obtains a first URL corresponding to the remote resource and secret data associated with the first URL. The first URL may be an intuitive URL with descriptive data about what the data at the remote resource means. The first URL may be obtained in various ways, such as by the user of the device typing a URL, by clicking a link from an email or other website, or by the device accessing a previously stored URL or a URL permanently embedded in the device. Using the secret data, the data processing device then generates an obscured URL for obtaining the actual location of the remote resource. The obscured URL is then used to access the remote resource.

Hence, the actual location of the remote resource is identified by the obscured URL, which may be any random string of characters (e.g. http://domain/a18b828f829e9 . . . ) which does not give away any personal information about the user or the user's devices. From the point of view of the cloud infrastructure, servers, and cloud providing or "big data" aggregating companies, the remote resource may be identified solely by the obscured URL, so that the URL does not give away sensitive information. Nevertheless, the first URL may be used by the data processing device to identify the remote resource. The first URL may be a more natural looking URL (e.g. http://domain/health/alicesmith/bloodpressure/ . . . ) which has a structure which allows authorized users of the remote resource to intuitively understand what the data at a particular URL represents and how the URL relates to other URLs, for example. The secret data allows the first URL to be mapped to the corresponding obscured URL at the data processing device so that the first URL need not be known to the network infrastructure.

The remote resource may correspond to any data or device accessed remotely by the data processing device. For example, the remote resource may comprise a data processing device or embedded system which can be controlled remotely from another platform; a remote computer, content aggregator, server or cloud platform which receives data posted by the data processing device; or a website or server accessed from the data processing device. The access to the remote resource may include writing data to the remote resource, reading data from the remote resource, and/or instructing a device associated with the remote resource to carry out an action, for example.

Data at the remote resource may be encrypted. For example, any data sent from the data processing device to the remote resource may be encrypted using an encryption key included with the secret data for the first URL. This means that both the URL identifying the remote resource and the data at the remote resource are obscured so that the network infrastructure or cloud operators have no visibility of any sensitive information associated with the resource. If the obscured URL is generated using a secret key, then the same key may be used for encrypting the data and generating the obscured URL, or different keys may be provided for generating the obscured URL and encrypted data respectively. Keys for encryption may be maintained locally at the device or obtained from another location.

In general, the first URL may be visible to a user of the data processing device. That is, the first URL may be the URL used by the user to identify the remote resource. However, the first URL does not necessarily need to be displayed on the data processing device itself. For example, a temperature sensor within a home heating system may be connected to the cloud so that temperature data can be posted to a remote resource identified by the obscured URL, but may not have a display on which the user can see the first URL. The user may have visibility of the first URL through a separate device such as a local heating controller within the user's home which communicates with the temperature sensor via wireless signals for example.

In many cases, the first URL may not identify any actual location of a remote resource on the network. Hence, if a device which cannot generate the obscured URL (e.g. it does not have the secret data for the first URL) tries to access the first URL, then the access will fail. For example, an http 404 error message may arise because the resource identified by the first URL cannot be found. By not providing any real location on the network corresponding to the first URL, security can be maintained.

It is also possible for the first URL to identify a real network location, but which corresponds to a different remote resource to the one accessed using the obscured URL, or to the same remote resource as the obscured URL. For example, different versions of content may be provided depending on whether the user has the secret key allowing the obscured URL to be generated. Also, in some cases the remote resource corresponding to the first URL may already be online identified by the first URL. For example, a legacy website designed without the use of the present technique may already have a URL containing intuitive information. If the legacy resource was suddenly moved to the location of the obscured URL to improve privacy/security, then the resource manager may lose users or customers who cannot find the old resource anymore. Therefore, it may be useful for the transition to the present technique to be made more gradually. At first, the legacy resource at the first URL may operate in parallel with the more secure resource at the obscured URL, so that the first URL will for a period correspond to a real network location. Once enough users/devices have been provided with the secret data which allows them to locate the obscured URL, the legacy resource can then be taken offline, at which point the first URL will no longer point to a real location.

It is desirable that the generation of the obscured URL from the secret data is such that the first URL cannot be obtained from the obscured URL using the secret data. That is, the secret data may contain enough information to allow the data processing device to generate the obscured URL corresponding to the first URL, but not enough information for a party to obtain the first URL from the obscured URL.

In some cases, the obscured URL may be generated by transforming the first URL into the obscured URL using the secret data. For example, the secret data may include a secret key and the obscured URL can be generated by encrypting the first URL using the key. For example, a one-way transformation, such as md5 or one of the SHA (Secure Hash Algorithm) family of transformations, may be used to hash the first URL based on a secret string contained in the secret data. Even if someone has the obscured URL and the secret string, it is not possible for them to determine the first URL used to generate the obscured URL.

It is also possible to generate the obscured URL based on information included in the secret data. The generation of the obscured URL may be independent of the particular character values of the first URL, i.e. the obscured URL is not a transformation of the first URL, but may be based solely on information included in the secret data. In this case, an attempt to access the first URL may trigger the obscured URL to be generated, but the first URL itself is not an input for the obscured URL generation. For example, the secret data could include the obscured URL itself, so that no transformation is required. Alternatively, the secret data could include one or more secret strings or values which can be transformed into the obscured URL. Either way, even if someone has the obscured URL and the secret data, this does not provide any information about the first URL.

Also, in some cases the secret data may be part of the first URL itself (e.g. a code or string of characters within the first URL), and the obscured URL may be generated by applying a hash or other transformation to the first URL. Also, the secret data may be data defining a hash algorithm to be applied to the first URL to generate the obscured URL. The secret data may be held locally by the device or may be obtained from a website or other remote resource.

Different data processing devices may be allocated different secret data corresponding to the same first URL. Therefore, when the different devices access the same first URL, this is mapped to different obscured URLs using the different secret data, so that different remote resources are accessed by the respective devices. This is very useful for allowing different content, or different representations of the same content, to be provided to different users or groups of users. Each user or group may use the same first URL and so may not be aware that they are given a different view of content to other users. The different obscured URLs may correspond to entirely different resources, or to different parts or subsets of a common remote resource. For example, it may be desirable to give some groups of users access to the entire resource, while other groups of users can only see selected sections of resource. Also, some users may be able to see high resolution data (e.g. full-size images or time series data sampled often) with other users seeing lower resolution data (e.g. compressed images or time series data sampled less frequently).

The obscured URL may identify the actual location of the remote resource to be accessed. Hence, once the obscured URL has been generated, the data processing device can simply access the location identified by the obscured URL.

However, if different versions of resource need to be made accessible to different users or groups of users, this approach may not be efficient as the resource manager may need to maintain multiple copies of data at different URLs, increasing the overhead associated with updating or maintaining the resource.

Therefore, it can be more efficient for the obscured URL to identify the location of a key node resource including data for obtaining a resource URL identifying the remote resource itself. Hence, the secret data maps the first URL to a corresponding obscured URL, which is used to access the key node resource. The key node resource then gives further data redirecting the device to the resource URL of the remote resource. The data at the key node resource may include the resource URL itself, data for calculating the resource URL, or data identifying another remote location from which the resource URL may be obtained, for example. Hence, if different representations of the resource are required for different users, each user can be provided with a different key node resource, but the different key nodes may direct the user to a common resource URL so that it is not necessary to maintain multiple versions of the remote resource itself. As for the obscured URL, the resource URL may also be a non-intelligible URL which does not contain sensitive information.

The key node resource may include information for decrypting data at the remote resource.

The key node resources can also simplify revocation of access to resources by users or groups of users. If the obscured URL directly identifies the remote resource, revoking a user's access may require the remote resource to be moved to a new location and new secret data provided to other users who need to continue accessing the resource to allow those users to generate the new obscured URL. This is a relatively complex operation.

A more efficient approach may be to provide key node resources identified by the obscured URLs generated using the different secret data for each user. To revoke access to a user or an entire group of users, the key node resource for that user or group of users is simply removed. This means that if the revoked user or a user of the revoked group attempts to access the remote resource, the obscured URL generated with the corresponding secret data will no longer map to a real location and so the access will fail preventing the real URL of the resource being accessed. This avoids the need to relocate the resource itself or to redistribute new secrets to authorized users.

The key node resources also simplify revocation of access to a resource for a selected user within a group while maintaining access to the resource for the rest of the group. This can be done by generating new group secret data for the selected group of users, providing access to the new secret data to the users of the group other than the selected user, creating a new key node resource identified by a new obscured URL generated using the new group secret data, the new key node resource comprising data for obtaining the resource URL of the remote resource, and making inaccessible the key node resource previously corresponding to the selected group of users. This means that the selected user who does not have the new secret data will not successfully reach a key node resource which allows access to a remote resource.

The secret data may be stored locally at the data processing device, or obtained from another location. The secret data may be referred to below as the "site secret" or "secret".

The same secret may be used for accessing more than one remote resource (e.g. a party may provide a single secret for accessing all URLs maintained by that party). Hence, when a device encounters a new URL, a new secret may also be supplied, but this is not essential since the device may already be in possession of a secret suitable for use with that URL.

The data processing device may be able to access multiple secrets corresponding to the same resource. For example, there may be different types of access permitted for different classes of user, and a single user may belong to several overlapping classes. For example a user may have a personal secret as well as a group secret corresponding to a group of users of which the user is a member and/or a generic secret which can be used by anyone. Multiple secrets may be stored locally at the data processing device.

An expansion URL can be provided to the data processing device (for example as part of the secret data for the first URL) identifying a location from which further secret data can be obtained. Using the expansion URL simplifies the distribution of group secrets, allowing secrets to be changed without having to directly contact each member of the group for example.

The data processing device can then attempt accesses to different obscured URLs generated with each of the secrets. In some cases the data processing device may try accessing one obscured URL, and if that does not succeed, try another obscured URL generated using a different secret, and continue trying until an access is successful or all of the secrets have been tried. For example, the secrets may have a predetermined secret hierarchy setting an order in which the data processing device should attempt to access the obscured URLs. For example, a personal secret may take precedence, followed by at least one group secret and then a generic secret. Alternatively, to improve performance the data processing device may attempt accesses to several devices simultaneously on the expectation that some accesses may fail (this may be faster than trying each in sequence). A similar hierarchy of secrets may determine which secret should be prioritized if multiple accesses are successful.

In some cases the secret key provided to the data processing device may have associated conditions for determining whether access to the remote resource may be granted using the secret data. For example, a secret scope may be defined identifying a domain, sub-domain, folder, or specified part of a site or collection of resources, for which the secret applies. In this case, accesses using the secret may fail if they are not within the scope parameter. The resource accessed using a particular secret may correspond to only part of an overall website or collection of resources, and other secrets may be required for other parts of the remote resource. Another example of an access condition included in the secret data may be a time constraint, so that the remote resource may only be accessed successfully within a specified time window or period.

Data stored at the remote resource or transactions sent to the resource may be cached at network nodes between the data processing device and the remote resource. For example, write transactions for writing data to the resource may be cached as they travel up the network. Since both the data and the URL of the remote resource can be made anonymous using the present technique, then this removes any risk of loss of privacy when the data is held by third parties. This frees up options for caching the data or transactions for the remote resource in multiple places, which can be very useful for performance or reliability reasons. For example, even if the remote resource itself is not available (e.g. a device may operate in a power-saving state most of the time and may only wake up periodically), its data may be read from a cache or proxy so that it is not necessary to wait for the resource to become available again. Also, if the data from the resource is available in multiple places then on accessing it the data can be obtained from the location with the lowest expected transaction cost (which may be determined based on time or energy for example). Similarly, when transactions are sent for the remote resource, and there are multiple communication channels available for a transaction then the channel with the lowest associated cost can be selected (e.g. one of Bluetooth, WiFi, 3G or wired connections may be selected).

Data and transactions may also be proxied at boundaries between different protocols (e.g. HTTP and COAP) or different communication mediums (e.g. Bluetooth and WiFi). If the data processing device and the device associated with the remote resource communicate using different protocols or mediums, a translating proxy (e.g. a router) may bridge the gap between them without loss of security/privacy.

The data processing device itself, or an intermediate network node between the data processing device and the remote resource, may have a transaction queue for queuing transactions to be sent to a device associated with the remote resource. The device associated with a remote resource may in some cases be the device providing the remote resource itself or may be another device which controls the remote resource. The device associated with the remote resource may pull the transactions from the transaction queue when it is ready to process the transactions. The transactions in the transaction queue may be encrypted to maintain security. The transaction queue is useful because it allows the data processing device and the device associated with the remote resource to communicate asynchronously. Even if the data processing device and device associated with the remote resource are not simultaneously in an active state, the data processing device can post transactions to the queue and the device associated with the remote resource can pull the transaction from the queue when it next wakes up.

Some devices may function both as a data processing device for accessing a remote resource and a device associated with a remote resource to be accessed by another device.

When instructing a specified operation to be performed using the remote resource, the data processing device may have to prove its identity, so that unauthorized devices cannot control the remote resource in inappropriate ways. Therefore, the data processing device may have, or be able to obtain, authentication information for verifying that the data processing has the right to instruct the specified operation to be performed using the remote resource. The authentication information may for example include a certificate and/or a public key associated with the data processing device which verifies the identity of the device sending the transaction. When receiving a transaction the device associated with the remote resource can then check the authentication information and verify whether the specified operation is allowed to be performed.

The authentication information may specify validity information specifying when the authentication information is valid (e.g. the authentication information's validity may expire at the end of a given time period). Also, the authentication information may define permission information specifying which operations are allowed to be instructed by the data processing device. This allows different access rights to be granted for different operations using the resource. For example, a device may be allowed to read data but not write.

In some cases the authentication information may be obtained by the device associated with the resource from an authentication URL specified in the transaction sent from the data processing device. Hence, the data processing device need not provide the authentication information itself, but may specify a location from which the authentication information can be maintained. For example, the authentication URL may belong to a certificate issuing authority. This approach makes it easier for relatively small data processing devices to control the remote resource, since it is not necessary for the data processing device to transmit certificates or other authentication information.

In some cases the authentication URL may be a URL identifying the data processing device itself, or may identify a different location.

The authentication URL may have a fingerprint portion which is generated using at least part of the authentication information held by the data processing device. This means that a device issuing a transaction for the remote resource can only succeed if it already has access to the authentication information, otherwise it will not be able to direct the device associated with the remote resource to the correct authentication URL for the authentication information. For example, the fingerprint may be a hash of part of the certificate of the authentication information, or a value encrypted using the public key. The fingerprint provides assurance that the correct version of the authentication information has been provided and has not been modified since it was authored. For example, if a party's website domain gets transferred to someone else, they cannot post a valid new version of "https://my-site/certs/geraint/12b274a" because the fingerprint will not match.

In some cases, there may be a chain of authentication information required to verify that a device is authorized to control the remote resource. For example, one certifying authority may certify another authority to issue certificates, and so parties authorized by the second authority may need to cite the certificates issued by both certificate authorities in order to be verified. In this case, the authentication URL fingerprint may be derived from each piece of authentication information in the chain, to ensure that only someone having all the links of the chain can be authenticated for controlling the resource.

The device associated with the remote resource may obtain the authentication information from the authentication URL via a different communication channel to the communication channel used to transmit the transaction. For instance, the data processing device may issue a transaction to a door device (acting as remote resource) by submitting a transaction over one channel (e.g. Bluetooth). The data processing device may cite the authentication URL in the transaction (e.g. https://abc.xyz.com/ufO7ZxhqJRwpI) so that the door device can obtain the authentication credentials. However, obtaining these credentials over Bluetooth from the device to the door in this way may be inefficient, slow or otherwise undesirable, so instead the door may uses some other unrelated route (e.g. house router, or a wired connection) to fetch the credentials.

The authentication information of the data processing device may be cached by at least one network node. The device associated with the remote resource can use the cached authentication information to verify that the data processing device has the right to instruct the specified operation to be performed using the remote resource. This allows authentication credentials to be obtained more quickly than if they always had to be sourced from the authentication URL. The node which caches the authentication information may belong to a different party to the party operating the authentication URL and the user of the data processing device.

The authentication information may separately define validity information specifying a time period when the authentication information is valid and cacheability information specifying a time period when the authentication information can be cached in the network. The cacheability information may specify a shorter period for caching than the period set in the validity information. This means that cached copies of the authentication information are discarded periodically while the authentication information remains valid, so that the authentication credentials will then need to be resourced from the original authentication URL. Access to a particular user can then be revoked easily by removing the authentication credentials for that user from the authentication URL. In contrast, if no limit on cached copies was set, then to revoke the right to control the remote resource one may need to set a shorter validity period, so that there is more management overhead in generating new authentication information and making this available to authorized users more frequently. Hence, the cacheability information helps to make management of authentication information more efficient.

Similarly, separate validity and cacheability information may also be defined for other cached resources. For example, a long lived piece of data, such as a device address, may also benefit from separate cacheability and validity periods to allow for revocation of access more frequently than new versions of the data are generated.

The periods specified by the validity information and the cacheability information may be any specified time or usage conditions. For example, the periods may be specified in seconds, minutes, hours, days, weeks, months, years, etc. The periods may have defined start and end times/dates/years or may only have an expiry time/date. The periods may also include non-continuous periods such as "every Monday until a certain date". Also, the periods may be based on the number of times the authentication information is used, rather than a time period (for example, valid for 100 accesses, cached copies discarded after 10 accesses).

The present technique may be implemented using at least one computer program executed by at least one device which controls the at least one device to perform the method as discussed above. The at least one program may be stored on at least one computer readable storage medium, which may be for example a non-transitory storage medium.

Viewed from another aspect, the present technique provides a data processing device comprising:

processing circuitry configured to perform data processing; and communication circuitry configured to access a remote resource;

wherein the processing circuitry is configured to:

(a) obtain a first uniform resource locator (URL) corresponding to the remote resource and obtain secret data corresponding to the first URL;

(b) generate an obscured URL using the secret data corresponding to the first URL, wherein the obscured URL is for obtaining the actual location of the remote resource; and (c) control the communication circuitry to access the remote resource using the obscured URL.

Viewed from a further aspect, the present technique provides a data processing device comprising:

processing means for performing data processing; and communication means for accessing a remote resource;

wherein the processing means is configured to:

(a) obtain a first uniform resource locator (URL) corresponding to the remote resource and obtain secret data corresponding to the first URL;

(b) generate an obscured URL using the secret data corresponding to the first URL, wherein the obscured URL is for obtaining the actual location of the remote resource; and (c) control the communication means to access the remote resource using the obscured URL.

Viewed from a further aspect, the present technique provides a method of providing a data processing device with access to a remote resource whose actual location is identified by a resource uniform resource locator (URL), the method comprising:

generating secret data corresponding to a user of the data processing device;

generating an obscured URL using the secret data corresponding to the user;

storing data for obtaining the resource URL to a location identified by the obscured URL; and providing the data processing device with (i) a first URL for identifying the remote resource to the user and (ii) the secret data for obtaining the obscured URL.

In a corresponding manner to the technique discussed above, a content author or party managing a remote resource may provide access to the resource for another user by generating secret data and obscured URL for the user, establishing a key node resource at the obscured URL to allow the user to obtain data for obtaining the actual resource URL, and provide the user's device with the first URL which the user can use to refer to the resource and the secret data for obtaining the obscured URL. By providing different users with different secret data and different obscured URLs, this allows the content author to provide user specific representations of content for each user.

Viewed from another aspect, the present technique provides a data processing device comprising:

processing circuitry configured to perform data processing; and communication circuitry configured to access remote locations;

wherein the processing circuitry is configured to:

(a) generate secret data corresponding to a user of a data processing device to be provided with access to a remote resource whose actual location is identified by a resource uniform resource locator (URL);

(b) generate an obscured URL using the secret data corresponding to the user; and (c) control the communication circuitry to store data for obtaining the resource URL to a location identified by the obscured URL, and to provide the data processing device with (i) a first URL for identifying the remote resource to the user and (ii) the secret data for obtaining the obscured URL.

Viewed from a further aspect, the present technique provides a data processing device comprising:

processing means for performing data processing; and communication means for accessing remote locations;

wherein the processing means is configured to:

(a) generate secret data corresponding to a user of a data processing device to be provided with access to a remote resource whose actual location is identified by a resource uniform resource locator (URL);

(b) generate an obscured URL using the secret data corresponding to the user; and (c) control the communication means to store data for obtaining the resource URL to a location identified by the obscured URL, and to provide the data processing device with (i) a first URL for identifying the remote resource to the user and (ii) the secret data for obtaining the obscured URL.

Although illustrative embodiments of the invention have been described in detail herein with reference to the accompanying drawings, it is to be understood that the invention is not limited to those precise embodiments, and that various changes and modifications can be effected therein by one skilled in the art without departing from the scope and spirit of the invention as defined by the appended claims.

The invention claimed is:

1. A method of accessing data sent between a remote resource and a data processing device, the method comprising:

caching data sent to the remote resource from the data processing device, at one or more intermediate network nodes between the data processing device and the remote resource, wherein the data sent to the intermediate network node is signed by the data processing device when the data sent to the remote resource is cached at the one or more intermediate network nodes, wherein the one or more intermediate network nodes is at least one of a gateway, network router, or internet service provider device; and verifying the signature of the data processing device prior to accessing the cached data stored at the one or more intermediate network nodes, wherein the signature of the data processing device comprises authentication information for verifying the identity of the data processing device;

wherein the cached data comprises an obscured uniform resource locator (URL) for obtaining the actual location of the remote resource, the obscured URL generated at the data processing device by using secret data corresponding to a first URL to transform the first URL to the obscured URL, wherein the first URL corresponds to a different location than the actual location of the remote resource; and accessing the cached data stored at the one or more intermediate network nodes using the obscured URL.

2. The method of claim 1, further comprising:

caching data uploaded from the remote resource at the one or more intermediate network nodes between the data processing device and the remote resource and accessing the cached data from a remote resource at the one or more intermediate network nodes using the obscured URL.

3. The method of claim 2, wherein the first URL is visible to the user of the data processing device.

4. The method of claim 2, wherein the first URL does not identify any actual location of a remote resource.

5. The method of claim 2, wherein the first URL identifies a location of a different remote resource to the remote resource accessed using the obscured URL.

6. The method of claim 2, wherein the obscured URL is generated by performing a transformation of the first URL into the obscured URL using the secret data.

7. The method of claim 2, wherein the obscured URL is generated based on the secret data corresponding to the first URL.

8. The method of claim 1, wherein if the cached data is available at a plurality of network nodes, then the cached data is obtained by the data processing device from one of the plurality of network nodes selected based on an expected transaction cost associated with obtaining the cached data from each network node.

9. The method of claim 1, wherein if the remote resource can be accessed using a plurality of communication channels, then the data processing device accesses the remote resource via one of the plurality of communication channels selected based on an expected transaction cost associated with each communication channel.

10. The method of claim 1, further comprising:

uploading data from the remote resource or sending data to the remote resource;

caching data uploaded from the remote resource at one or more intermediate network nodes between the data processing device and the remote resource when uploading data from the remote resource; and signing the data with a secret key upon uploading or sending.

11. The method of claim 10, wherein the remote resource signs the data when uploading the data.

12. The method of claim 1, further comprising sending the data to the remote resource for instructing a specified operation to be performed using the remote resource, the data processing device having or obtaining authentication information for verifying that the data processing device has the right to instruct the specified operation to be performed using the remote resource.

13. The method of claim 1, wherein the accessing includes the data processing device having or obtaining authentication information for verifying that the data processing device has the right to access the cached data.

14. The method of claim 13, wherein obtaining authentication information for verifying that the data processing device has the right to access the cached data includes a shared secret between the data processing device and the remote resource.

15. The method of claim 1, further comprising:

uploading the data from the one or more intermediate network nodes to a remote cloud server, wherein the server signs the data when the data is successfully stored at the cloud server.

16. The method of claim 15, wherein the cloud server signs the data only when the remote resource is an authorized remote resource.

17. The method of claim 1, further comprising accessing the cached data stored at the one or more intermediate network nodes and wherein the accessing includes the data processing device having or obtaining authentication information for verifying that the data processing device has the right to access the cached data.

18. A data processing device comprising:

processing circuitry configured to perform data processing; and communication circuitry configured to access a remote resource;

wherein the processing circuitry is configured to:

access cached data stored at one or more intermediate network nodes between the data processing device and the remote resource, wherein the one or more intermediate network nodes is at least one of a gateway, network router, or internet service provider device, the cached data having been data sent to the remote resource from the data processing device, the data sent to the one or more intermediate network nodes being signed by the data processing device with a signature when the data is sent to the remote resource, wherein the signature of the data processing device is verified prior to the cached data being accessed, and wherein the signature of the data processing device comprises authentication information for verifying the identity of the data processing device, wherein the cached data comprises an obscured uniform resource locator (URL) for obtaining the actual location of the remote resource, the obscured URL generated at the data processing device by using secret data corresponding to a first URL to transform the first URL to the obscured URL, wherein the first URL corresponds to a different location than the actual location of the remote resource, and access the cached data stored at the one or more intermediate network nodes using the obscured URL.

19. An intermediate network node between a data processing device and a remote resource comprising:

processing circuitry configured to perform data processing;

communication circuitry configured to provide access between the data processing device and the remote resource;

and a memory store configured to store cached data, wherein the processing circuitry is configured to cache data sent to the remote resource from the data processing device during communication between the data processing device and the remote resource, wherein the data sent to the intermediate network node is signed by the data processing device with a signature when the data sent to the remote resource is cached at the intermediate network node, and wherein the signature of the data processing device comprises authentication information for verifying the identity of the data processing device, wherein the cached data comprises an obscured uniform located (URL) for obtaining the actual location of the remote resource, the obscured URL generated at the processing device by using secret data corresponding to a first URL to transform the first URL to the obscured URL, wherein the first URL corresponds to a different location than the actual location of the remote resource, wherein the processing circuitry is configured to allow access to the cached data stored at the one or more intermediate network nodes using the obscured URL, and wherein the intermediate network node is at least one of a gateway, network router, or internet service provider device.

* * * * *